US012655204B2

(12) United States Patent
Wan et al.

(10) Patent No.: US 12,655,204 B2
(45) Date of Patent: Jun. 16, 2026

(54) ANTI-VEGF SINGLE-DOMAIN ANTIBODY AND USE THEREOF

(71) Applicant: SHANGHAI NOVAMAB BIOPHARMACEUTICALS CO., LTD., Shanghai (CN)

(72) Inventors: Yakun Wan, Shanghai (CN); Min Zhu, Shanghai (CN); Junwei Gai, Shanghai (CN); Xiaoning Shen, Shanghai (CN)

(73) Assignee: SHANGHAI NOVAMAB BIOPHARMACEUTICALS CO., LTD., Shanghai (CN)

( * ) Notice: Subject to any disclaimer, the term of this patent is extended or adjusted under 35 U.S.C. 154(b) by 1116 days.

(21) Appl. No.: 17/640,083

(22) PCT Filed: Mar. 10, 2020

(86) PCT No.: PCT/CN2020/078595
§ 371 (c)(1),
(2) Date: Mar. 3, 2022

(87) PCT Pub. No.: WO2021/042694
PCT Pub. Date: Mar. 11, 2021

(65) Prior Publication Data
US 2022/0324954 A1 Oct. 13, 2022

(30) Foreign Application Priority Data

Sep. 3, 2019 (CN) .......................... 201910829413.3

(51) Int. Cl.
| | |
|---|---|
| *A61K 39/395* | (2006.01) |
| *C07K 16/22* | (2006.01) |
| *G01N 33/575* | (2026.01) |
| *A61K 39/00* | (2006.01) |

(52) U.S. Cl.
CPC ......... *C07K 16/22* (2013.01); *G01N 33/5758* (2026.01); *A61K 2039/505* (2013.01); *C07K 2317/24* (2013.01); *C07K 2317/565* (2013.01); *C07K 2317/569* (2013.01); *C07K 2317/73* (2013.01)

(58) Field of Classification Search
None
See application file for complete search history.

(56) References Cited

U.S. PATENT DOCUMENTS

| | | |
|---|---|---|
| 7,740,844 B2 | 6/2010 | Hong et al. |
| 2009/0269336 A1 | 10/2009 | Hong et al. |
| 2013/0078248 A1 | 3/2013 | Gschwind et al. |

FOREIGN PATENT DOCUMENTS

| | | |
|---|---|---|
| CN | 103209995 A | 7/2013 |
| CN | 103893759 A | 7/2014 |
| CN | 105820244 A | 8/2016 |
| CN | 110105450 A | 8/2019 |
| CN | 110452297 A | 11/2019 |
| JP | 2010518839 A | 6/2010 |
| JP | 2011505135 A | 2/2011 |
| JP | 2013506411 A | 2/2013 |
| JP | 2013541939 A | 11/2013 |

OTHER PUBLICATIONS

Muyldermans and Lauwereys (Journal of Molecular Recognition, 1999. vol. 12, pp. 131-140).*
Konning et al. (Curr. Opin. Struct. Bio. 45: 10-16, 2017).*
Harmsen and Haard (Applied Microbiology and Biotechnology, 2007. vol. 77, pp. 13-22).*
Saerens et al. (J. Mol. Biol. 352:597-607, 2005).*
Rudikoff, et al. (Proceedings of the National Academy of Sciences, 1982. vol. 79, p. 1979).*
Noel et al. Biochimie 131: 11-19, 2016.*
Ebrahimizadeh, Walead et al.; "Production of Novel VHH Nanobody Inhibiting Angiogenesis by Targeting Binding Site of VEGF"; Applied Biochemistry and Biotechnology; vol. 176, No. 7; Aug. 1, 2015; pp. 1985-1995; ISSN: 0273-2289.
Freund, K. Bailey et al.: "Aflibercept: a review of its use in the treatment of choroidal neovascularization due to age-related macular degeneration"; Clinical Ophthalmology, vol. 2015, No. 9; Dec. 1, 2015; pp. 2355-2371.
"Notice of Reasons for Refusal for Application No. JP2022-514739"; Japan Patent Office; Mar. 28, 2023, pp. 1-3.

* cited by examiner

*Primary Examiner* — Christine J Saoud
(74) *Attorney, Agent, or Firm* — NKL Law; Bin Lu; Allen Xue

(57) ABSTRACT

An anti-VEGF single-domain antibody and a VHH chain thereof have been described. A coding sequence for coding the single-domain antibody or the VHH chain thereof, a corresponding expression vector, a host cell capable of expressing the single-domain antibody, and a production method for the single-domain antibody have been presented. The single-domain antibody can specifically recognize human VEGFA and will not cause cross reactions with VEGFB, VEGFC and VEGFD, thus having a good specificity. The single-domain antibody can further recognize VEGFAs of a human, a rat, a rabbit and a monkey, effectively blocks interactions between VEGFA and VEGFR2 and between VEGFA and VEGFR1, has an excellent inhibiting effect on angiogenesis, and has a good stability in a non-preparation condition.

13 Claims, 8 Drawing Sheets

Specification includes a Sequence Listing.

ELISA: hVEGFA and hVEGFR2 interaction blocking

| Abs | IC50 (ug/ml) |
|-----|--------------|
| Nb24 | 0.015 |
| AVASTIN® | 0.217 |

Inhibition of HUVEC cells proliferation

| Abs | IC50 (ng/ml) |
|-----|--------------|
| Nb24 | 29.58 |
| AVASTIN® | 72.28 |

ELISA: hVEGFA and hVEGFR2 interaction blocking concentration（ug/ml）

| Abs | IC50（ug/ml） |
|---|---|
| huNb24 | 0.038 |
| Nb24 | 0.045 |

ELISA: hVEGFA and hVEGFR2 interaction blocking

| Abs | IC50 (ug/ml) |
|---|---|
| hu bi-Nb24(Y) | 0.013 |
| huNb24 | 0.044 |
| AVASTIN® | 0.331 |

ELISA: hVEGFA and hVEGFR2 interaction blocking

| Abs | IC50 (ug/ml) |
|---|---|
| hu bi-Nb24(Y) | 0.022 |
| EYLEA® | 0.085 |
| Conbercept | 0.088 |
| AVASTIN® | 0.439 |

Inhibition of HUVEC cells proliferation

| Abs | IC50 (ng/ml) |
|---|---|
| hu bi-Nb24(Y) | 53.59 |
| EYLEA® | 65.96 |
| Conbercept | 129.7 |
| AVASTIN® | 254.7 |

Binding different VEGF family members

| Abs | IC50 （ug/ml） |
|---|---|
| hu bi-Nb24(Y) | 0.168 |
| AVASTIN® | 0.967 |

SEQUENCE LISTING

<160> NUMBER OF SEQ ID NOS: 20

<210> SEQ ID NO 1
<211> LENGTH: 10
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain CDR1

<400> SEQUENCE: 1

Gly Phe Thr Phe Asp Asp Pro Asp Val Gly
1               5                   10

<210> SEQ ID NO 2
<211> LENGTH: 7
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain CDR2

<400> SEQUENCE: 2

Ile Ser Lys Asp Gly Ser Thr
1               5

<210> SEQ ID NO 3
<211> LENGTH: 19
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain CDR3

<400> SEQUENCE: 3

Ala Ala Asp Ser Asn Pro Ile Ala Pro Ile Arg Thr Cys Leu Gly Trp
1               5                   10                  15

Tyr Asn Tyr

<210> SEQ ID NO 4
<211> LENGTH: 25
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR1

<400> SEQUENCE: 4

Gln Val Gln Leu Gln Glu Ser Gly Gly Gly Ser Val Gln Ala Gly Gly
1               5                   10                  15

Ser Leu Arg Leu Ser Cys Thr Ala Ser
            20                  25

<210> SEQ ID NO 5
<211> LENGTH: 15
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR2

<400> SEQUENCE: 5

Trp Phe Arg Gln Ala Pro Gly Asn Glu Cys Glu Leu Val Ser Thr
1               5                   10                  15

<210> SEQ ID NO 6
<211> LENGTH: 38
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR3

<400> SEQUENCE: 6

Tyr Tyr Thr Asp Ser Val Lys Gly Arg Phe Thr Ile Ser Gln Asp Tyr
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 7
<211> LENGTH: 11
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR4

<400> SEQUENCE: 7

Trp Gly Gln Gly Thr Gln Val Thr Val Ser Ser
1               5                   10

<210> SEQ ID NO 8
<211> LENGTH: 125
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain

<400> SEQUENCE: 8

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Pro
            20                  25                  30

Asp Val Gly Trp Phe Arg Gln Ala Pro Gly Asn Glu Cys Glu Leu Val
            35                  40                  45

Ser Thr Ile Ser Lys Asp Gly Ser Thr Tyr Tyr Thr Asp Ser Val Lys
    50                  55                  60

Gly Arg Phe Thr Ile Ser Gln Asp Tyr Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Ser Asn Pro Ile Ala Pro Ile Arg Thr Cys Leu Gly Trp Tyr
            100                 105                 110

Asn Tyr Trp Gly Gln Gly Thr Gln Val Thr Val Ser Ser
        115                 120                 125
```

<210> SEQ ID NO 9
<211> LENGTH: 377
<212> TYPE: DNA
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain

<400> SEQUENCE: 9

```
caggtgcagc tgcaggagtc tggaggaggc tcggtgcagg ctggagggtc tctgagactc      60
tcctgtacag cctctggatt cacttttgat gatcctgacg tgggctggtt ccgccaggct     120
ccagggaatg agtgcgagtt ggtctcaact attagtaagg atggtagtac atactataca     180
gactccgtga agggccgatt caccatctcc aagactacg ccaagaacac ggtgtatctg      240
caaatgaaca gcctgaaacc tgaggacacg gccgtgtatt actgtgcggc agactccaat     300
cctatagcgc ctattagaac ttgtttgggg tggtataact actggggcca ggggacccag     360
gtcaccgtct cctcagc                                                     377
```

<210> SEQ ID NO 10
<211> LENGTH: 25
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR1

<400> SEQUENCE: 10

```
Glu Val Gln Leu Gln Glu Ser Gly Gly Gly Leu Val Gln Pro Gly Gly
```

-continued

```
1               5               10              15

Ser Leu Arg Leu Ser Cys Thr Ala Ser
            20              25

<210> SEQ ID NO 11
<211> LENGTH: 15
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR2

<400> SEQUENCE: 11

Trp Phe Arg Gln Ala Pro Gly Asn Glu Cys Glu Leu Val Ser Thr
1               5               10              15

<210> SEQ ID NO 12
<211> LENGTH: 38
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR3

<400> SEQUENCE: 12

Tyr Tyr Thr Asp Ser Val Lys Gly Arg Phe Thr Ile Ser Arg Asp Tyr
1               5               10              15

Ala Lys Asn Thr Val Tyr Leu Gln Met Asn Ser Leu Arg Ala Glu Asp
            20              25              30

Thr Ala Val Tyr Tyr Cys
        35

<210> SEQ ID NO 13
<211> LENGTH: 11
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR4

<400> SEQUENCE: 13

Trp Gly Gln Gly Thr Leu Val Thr Val Ser Ser
1               5               10

<210> SEQ ID NO 14
<211> LENGTH: 125
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain

<400> SEQUENCE: 14

Glu Val Gln Leu Gln Glu Ser Gly Gly Gly Leu Val Gln Pro Gly Gly
1               5               10              15

Ser Leu Arg Leu Ser Cys Thr Ala Ser Gly Phe Thr Phe Asp Asp Pro
            20              25              30

Asp Val Gly Trp Phe Arg Gln Ala Pro Gly Asn Glu Cys Glu Leu Val
```

```
          35                40                45
Ser Thr Ile Ser Lys Asp Gly Ser Thr Tyr Tyr Thr Asp Ser Val Lys
    50                55                60

Gly Arg Phe Thr Ile Ser Arg Asp Tyr Ala Lys Asn Thr Val Tyr Leu
65                70                75                80

Gln Met Asn Ser Leu Arg Ala Glu Asp Thr Ala Val Tyr Tyr Cys Ala
                85                90                95

Ala Asp Ser Asn Pro Ile Ala Pro Ile Arg Thr Cys Leu Gly Trp Tyr
            100               105               110

Asn Tyr Trp Gly Gln Gly Thr Leu Val Thr Val Ser Ser
        115               120               125

<210> SEQ ID NO 15
<211> LENGTH: 375
<212> TYPE: DNA
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain

<400> SEQUENCE: 15
gaggtgcagc tgcaggagag cggcggcggc ctggtgcagc ccggcggcag cctgaggctg      60
agctgcaccg ccagcggctt caccttcgac gaccccgacg tgggctggtt caggcaggcc     120
cccggcaacg agtgcgagct ggtgagcacc atcagcaagg acggcagcac ctactacacc     180
gacagcgtga aggcaggtt caccatcagc agggactacg ccaagaacac cgtgtacctg     240
cagatgaaca gcctgaggggc cgaggacacc gccgtgtact actgcgccgc cgacagcaac     300
cccatcgccc ccatcaggac ctgcctgggc tggtacaact actggggcca gggcaccctg     360
gtgaccgtga gcagc                                                     375

<210> SEQ ID NO 16
<211> LENGTH: 259
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: anti-VEGF antibody

<400> SEQUENCE: 16

Glu Val Gln Leu Gln Glu Ser Gly Gly Gly Leu Val Gln Pro Gly Gly
1               5                10                15

Ser Leu Arg Leu Ser Cys Thr Ala Ser Gly Phe Thr Phe Asp Asp Pro
            20                25                30

Asp Val Gly Trp Phe Arg Gln Ala Pro Gly Asn Glu Cys Glu Leu Val
        35                40                45

Ser Thr Ile Ser Lys Asp Gly Ser Thr Tyr Tyr Thr Asp Ser Val Lys
    50                55                60

Gly Arg Phe Thr Ile Ser Arg Asp Tyr Ala Lys Asn Thr Val Tyr Leu
65                70                75                80

Gln Met Asn Ser Leu Arg Ala Glu Asp Thr Ala Val Tyr Tyr Cys Ala
                85                90                95

Ala Asp Ser Asn Pro Ile Ala Pro Ile Arg Thr Cys Leu Gly Trp Tyr
            100               105               110

Asn Tyr Trp Gly Gln Gly Thr Leu Val Thr Val Ser Ser Gly Gly Gly
```

-continued

```
            115              120              125
Gly Ser Gly Gly Gly Ser Glu Val Gln Leu Gln Glu Ser Gly Gly Gly
    130              135              140
Leu Val Gln Pro Gly Gly Ser Leu Arg Leu Ser Cys Thr Ala Ser Gly
145              150              155              160
Phe Thr Phe Asp Asp Pro Asp Val Gly Trp Phe Arg Gln Ala Pro Gly
                165              170              175
Asn Glu Cys Glu Leu Val Ser Thr Ile Ser Lys Asp Gly Ser Thr Tyr
            180              185              190
Tyr Thr Asp Ser Val Lys Gly Arg Phe Thr Ile Ser Arg Asp Tyr Ala
            195              200              205
Lys Asn Thr Val Tyr Leu Gln Met Asn Ser Leu Arg Ala Glu Asp Thr
    210              215              220
Ala Val Tyr Tyr Cys Ala Ala Asp Ser Asn Pro Ile Ala Pro Ile Arg
225              230              235              240
Thr Cys Leu Gly Trp Tyr Asn Tyr Trp Gly Gln Gly Thr Leu Val Thr
                245              250              255
Val Ser Ser
```

<210> SEQ ID NO 17
<211> LENGTH: 777
<212> TYPE: DNA
<213> ORGANISM: Artificial sequence
<220> FEATURE:
<223> OTHER INFORMATION: synthesized
<220> FEATURE:
<221> NAME/KEY: misc_feature
<223> OTHER INFORMATION: anti-VEGF antibody

<400> SEQUENCE: 17

```
gaagttcaac ttcaagagtc tggtggtggt ttagttcaac caggtgggtc tttgagattg      60
tcttgtactg cttctggttt tactttgat gatccagatg ttggttggtt tagacaagct     120
ccaggtaatg aatgtgaatt agtttctact atttctaagg atggttctac ttactacact     180
gactctgtta agggtagatt cactatttcc agagattacg ctaagaacac tgtttacttg     240
caaatgaact ctttgagagc tgaagatact gctgtttact actgtgctgc tgattccaat     300
ccaattgctc caattagaac ttgtttggga tggtacaact actggggtca aggtactttg     360
gttactgttt cttctggtgg tggaggttct ggaggtggtt ctgaagttca attgcaagaa     420
tctggtggtg gtttggttca accaggtggt tctttgagat tgtcttgtac tgcttctgga     480 ttcactttg atgatccaga tgttggttgg tttagacaag ctccaggtaa tgaatgtgaa     540
ttggtttcta ctatttctaa ggatggtagt acttactaca ctgattctgt taagggtagg     600
tttactattt ccagagatta cgcaaagaac accgtctact gcaaatgaa ctctttgaga     660 gctgaggata ctgctgtcta ctactgtgct gctgattcca acccaatcgc tccaatcaga     720
acctgtttgg gttggtacaa ctactggggt caaggtactt tggtcactgt ttcctct       777
```

<210> SEQ ID NO 18
<211> LENGTH: 9
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: linker

<400> SEQUENCE: 18

-continued

```
Gly Gly Gly Gly Ser Gly Gly Gly Ser
1               5

<210> SEQ ID NO 19
<211> LENGTH: 2
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: linker

<400> SEQUENCE: 19

Gly Ser
1

<210> SEQ ID NO 20
<211> LENGTH: 5
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: linker

<400> SEQUENCE: 20

Gly Gly Gly Gly Ser
1               5
```

ANTI-VEGF SINGLE-DOMAIN ANTIBODY AND USE THEREOF

INCORPORATION OF SEQUENCE LISTING

This application contains a sequence listing in Computer Readable Form (CRF). The CFR file containing the sequence listing entitled "PBA4085327-SequenceListing.txt", which was created on Mar. 3, 2022, and is 11,886 bytes in size. The information in the sequence listing is incorporated herein by reference in entirety.

TECHNICAL FIELD

The present invention relates to the technical field of biomedicine or bio-pharmaceuticals, and more particularly relates to an anti-VEGF single-domain antibody and use thereof.

BACKGROUND

Current vascular endothelial growth factor drugs include Bevacizumab (trade name AVASTIN®), Conbercept, Aflibercept, etc. On Feb. 13, 2018, China Food and Drug Administration (CFDA) approved the use of EYLEA® (Aflibercept intraocular injection solution) in the treatment of the adult diabetic macular edema. The price of Bevacizumab (trade name AVASTIN®) for anti-tumor treatment is 1998 RMB per vial of 4 ml (containing 100 mg Bevacizumab), and the recommended dose is 5 mg/kg, administrated once every 14 days. If a patient's body weight is 60 kg, 300 mg Bevacizumab should be administered each time, so that there are three bottles, administrated two times a month, and price is 11988 RMB per month. The price of Conbercept for treatment of ophthalmic diseases is 5550 RMB per 0.2 mL (containing 10 mg Conbercept), and its administration regime is to inject once a month in the first three months and once in the subsequent three months, totally 6 times a year with a price of 33000 RMB per year. In addition, the price of the Aflibercept is 5850 RMB per bottle of 0.1 ml (containing 4 mg Aflibercept), and its administration regime is to administrate once every two months, totally 6 times a year with a price of 35100 RMB per year.

Single-domain antibody (NANOBODY®, Nb) is heavy chain single-domain antibody VHH (variable domain of heavy-chain antibody). Camels have a heavy-chain antibody (HCAb) that naturally lacks the light chain. The single-domain antibody obtained by cloning its variable region, is consisted of only one heavy chain variable region and is the smallest unit of fully functional stable binding antigen at present. Single-domain antibodies have the characteristics of high stability, good aqueous solubility, simple humanization, high targeting and strong penetration, and play a huge role in immune experiment, diagnosis and treatment. Single-domain antibodies are gradually becoming a new force in the diagnosis and treatment of new generation of antibodies.

It has become an urgent problem to be solved to develop a new single-domain anti-VEGF antibody with better specificity, blocking efficacy, and simple production, so as to reduce the production cost and lighten the medication burden of patients.

SUMMARY OF INVENTION

The purpose of the present invention is to provide an anti-VEGF single-domain antibody and use thereof.

Specifically, the purpose of the present invention is to provide a single-domain antibody with better specificity that can effectively block the interaction between VEGFA and VEGFR2, VEGFA and VEGFR1, has a good inhibitory effect on the angiogenesis and has a good inhibitory activity on solid tumors.

In the first aspect of the present invention, it provides a complementarity determining region CDR region of an anti-VEGF single-domain antibody VHH chain, wherein the complementarity determining regions or CDRs of the VHH chain comprise CDR1 as shown in SEQ ID NO: 1, CDR2 as shown in SEQ ID NO: 2, and CDR3 as shown in SEQ ID NO: 3.

In another preferred embodiment, the CDR1, CDR2 and CDR3 are separated by the framework regions FR1, FR2, FR3 and FR4.

In the second aspect of the present invention, it provides a VHH chain of an anti-VEGF single-domain antibody, wherein the VHH chain comprises the framework regions or FRs and the complementarity determining regions or CDRs according to the first aspect of the present invention, In another preferred embodiment, wherein the framework regions or FRs comprise:

(a) FR1 as shown in SEQ ID NO: 4, FR2 as shown in SEQ ID NO: 5, FR3 as shown in SEQ ID NO: 6, and FR4 as shown in SEQ ID NO: 7; or (b) FR1 as shown in SEQ ID NO: 10, FR2 as shown in SEQ ID NO: 11, FR3 as shown in SEQ ID NO: 12, and FR4 as shown in SEQ ID NO: 13.

In another preferred embodiment, the VHH chain of the anti-VEGF single-domain antibody is as shown in SEQ ID NO: 8 or 14.

In addition, it further provides a novel heavy chain variable region of the anti-VEGF single-domain antibody, wherein the heavy chain variable region comprises CDR1 as shown in SEQ ID NO: 1, CDR2 as shown in SEQ ID NO: 2, and CDR3 as shown in SEQ ID NO: 3.

In the third aspect of the present invention, it provides an anti-VEGF antibody, wherein the anti-VEGF antibody has a VHH chain according to the second aspect of the present invention.

In another preferred embodiment, the anti-VEGF antibody includes double-chain antibody, single-chain antibody, or single-domain antibody.

In another preferred embodiment, the anti-VEGF antibody is selected from the group consisting of animal derived antibody, chimeric antibody, and humanized antibody; more preferably is humanized antibody, human-animal chimeric antibody, most preferably is fully humanized antibody.

In another preferred embodiment, the anti-VEGF antibody can be antibody fragments, such as Fab, Fab', $(Fab')_2$ or other antibody derivatives known in the art, and can be any one or more of IgA, IgD, IgE, IgG and IgM antibody or other subtypes thereof.

In another preferred embodiment, the anti-VEGF antibody is anti-VEGF single domain antibody.

In another preferred embodiment, the anti-VEGF antibody includes monomer, bivalent antibody and/or multivalent antibody.

In another preferred embodiment, the anti-VEGF antibody includes one or more VHH chains of amino acid sequences as shown in SEQ ID NO: 8 or SEQ ID NO: 14.

In another preferred embodiment, the VHH chain sequence of the anti-VEGF antibody is shown as SEQ ID NO: 8 or SEQ ID NO: 14.

In another preferred embodiment, the anti-VEGF antibody comprises two VHH chains of amino acid sequences as shown in SEQ ID NO: 8 or SEQ ID NO: 14.

In another preferred embodiment, the anti-VEGF antibody has VHH chains of amino acid sequences as shown in SEQ ID NO: 8 and/or SEQ ID NO: 14.

In another preferred embodiment, the two VHH chains of amino acid sequences as shown in SEQ ID NO: 14 are linked via a linker.

In another preferred embodiment, the linker is selected from the following sequences: $(G_aS_b)_x$-$(G_mS_n)_y$, wherein each of a, b, m, n, x, y is 0 or 1 or 1 or 2 or 3 or 4 or 5 or 6 or 7 or 8 or 9 or 10 (more preferably, a=4, while b=1, m=3, and n=1).

In another preferred embodiment, the linker is selected from the group consisting of GGGGSGGGS (SEQ ID NO: 18), GS (SEQ ID NO: 19), GGGGS (SEQ ID NO: 20).

In another preferred embodiment, the amino acid sequence of the anti-VEGF antibody is shown as SEQ ID NO: 16.

In another preferred embodiment, the bivalent anti-VEGF antibody is hu bi-Nb24(Y).

In the fourth aspect of the present invention, it provides a polynucleotide encoding a protein selected from the group consisting of: the CDR region of the anti-VEGF single-domain antibody VHH chain according to the first aspect of the present invention, the VHH chain of the anti-VEGF single-domain antibody according to the second aspect of the present invention, and the anti-VEGF single-domain antibody according to the third aspect of the present invention.

In another preferred embodiment, the polynucleotide has a nucleotide sequence as shown in SEQ ID NO: 9, or 15.

In another preferred embodiment, the polynucleotide has a nucleotide sequence as shown in SEQ ID NO: 17.

In another preferred embodiment, the polynucleotide comprises DNA or RNA.

In the fifth aspect of the present invention, it provides an expression vector containing the polynucleotide according to the fourth aspect of the present invention.

In another preferred embodiment, the expression vector is selected from the group consisting of DNA, RNA, viral vector, plasmid, transposon, other gene transfer system, and a combination thereof.

Preferably, the expression vector comprises viral vector, such as lentivirus, adenovirus, AAV virus, retrovirus, and a combination thereof.

In the sixth aspect of the present invention, it provides a host cell containing the expression vector according to the fifth aspect of the present invention, or in which the polynucleotide according to the fourth aspect of the present invention is integrated into a genome thereof.

In another preferred embodiment, the host cell comprises a prokaryotic cell or an eukaryotic cell.

In another preferred embodiment, the host cell is selected from the group consisting of: *E. coli*, a yeast cell, a mammalian cell, bacteriophage, and a combination thereof.

In another preferred embodiment, the prokaryotic cell is selected from the group consisting of: *Escherichia coli, Bacillus subtilis, Lactobacillus, Streptomyces, Proteus mirabilis*, and a combination thereof.

In another preferred embodiment, the eukaryotic cell is selected from the group consisting of: *Pichia pastoris, Saccharomyces cerevisiae, Schizosaccharomyces pombe, Trichoderma*, and a combination thereof.

In another preferred embodiment, the eukaryotic cell is selected from the group consisting of: an insect cell such as a grass armyworm cell, a plant cell such as a tobacco cell, a BHK cell, a CHO cell, a COS cell, a myeloma cell, and a combination thereof.

In another preferred embodiment, the host cell is preferably a mammalian cell, and more preferably an HEK293 cell, CHO cell, BHK cell, NSO cell, or COS cell.

In another preferred embodiment, the host cell is *Pichia pastoris*.

In the seventh aspect of the present invention, it provides a method for producing an anti-VEGF single-domain antibody, comprising the steps of:

(a) cultivating the host cell according to the sixth aspect of the present invention under conditions suitable for production of a single-domain antibody, thereby obtaining a culture containing the anti-VEGF single-domain antibody; and (b) isolating or recovering the anti-VEGF single-domain antibody or the Fc fusion protein thereof from the culture; and (c) optionally, purifying and/or modifying the VEGF single-domain antibody in the step(b).

In another preferred embodiment, the anti-VEGF single-domain antibody has an amino acid sequence as shown in SEQ ID NO: 8 or 14.

In another preferred embodiment, the anti-VEGF single-domain antibody has an amino acid sequence as shown in SEQ ID NO: 16.

In the eighth aspect of the present invention, it provides an immunoconjugate containing:

(a) the VHH chain of the anti-VEGF single-domain antibody according to the second aspect of the present invention, or the anti-VEGF single-domain antibody according to the third aspect of the present invention; and (b) a coupling moiety selected from the group consisting of: a detectable label, drug, toxin, cytokine, radionuclide, enzyme, gold nanoparticle/nanorod, magnetic nanoparticle, viral capsid protein or VLP, and a combination thereof.

In another preferred embodiment, the radionuclide comprises:

(i) a diagnostic isotope which is selected from the group consisting of Tc-99m, Ga-68, F-18, I-123, I-125, I-131, In-111, Ga-67, Cu-64, Zr-89, C-11, Lu-177, Re-188, and a combination thereof; and/or (ii) a therapeutic isotope which is selected from the group consisting of Lu-177, Y-90, Ac-225, As-211, Bi-212, Bi-213, Cs-137, Cr-51, Co-60, Dy-165, Er-169, Fm-255, Au-198, Ho-166, I-125, I-131, Ir-192, Fe-59, Pb-212, Mo-99, Pd-103, P-32, K-42, Re-186, Re-188, Sm-153, Ra223, Ru-106, Na24, Sr89, Tb-149, Th-227, Xe-133, Yb-169, Yb-177, and a combination thereof.

In another preferred embodiment, the coupling moiety is a drug or toxin.

In another preferred embodiment, the coupling moiety is a cytotoxic drug.

In another preferred embodiment, the cytotoxic drug is selected from the group consisting of an antitubulin drug, DNA sulcus binding reagent, DNA replication inhibitor, alkylation reagent, antibiotic, folic acid antagonist, antimetabolite, chemotherapeutic sensitizer, topoisomerase inhibitor, vinca alkaloids, and a combination thereof.

In another preferred embodiment, the particularly useful cytotoxic drug includes, for example, DNA sulcus binding reagent, DNA alkylation reagent, and tubulin inhibitor. The typical cytotoxic drug includes, such as auristatins, camptothecins, duocarmycins, etoposides, maytansines and maytansinoids (such as DM1 and DM4), taxanes, benzodiaz-epines or benzodiazepine containing drugs (such as PBDs, indolinobenzodiazepines and oxazolidinobenzodiazepines), vinca alkaloids, and a combination thereof.

In another preferred embodiment, the toxin is selected from the group consisting of otostatins (e.g., otostatin E, otostatin F, MMAE and MMAF), aureomycin, metametanol, ricin toxin, ricin A-chain, cobustatin, docamicin, dorastatin, doxorubicin, daunorubicin, paclitaxel, cisplatin, cc1065, ethidium bromide, mitomycin, etoposide, tenoposide, vincristine, vinblastine, colchicine, dihydroxy anthrax dione, actinomycin, diphtheria toxin, *Pseudomonas* ecto-toxin (PE)A, PE40, Acacia bean toxin, Acacia bean toxin A chain, capsule root toxin A chain, α-tocsin, Atractylodes toxin, mitogellin, retstrictocin, phenomycin, enomycin, curi-cin, battocin, Kazinomycin, *Sapaonaria Officinalis* inhibi-tor, glucocorticoids, and a combination thereof.

In another preferred embodiment, the coupling moiety is a detectable label.

In another preferred embodiment, the coupling moiety is selected the group consisting of a fluorescent or luminescent marker, radioactive marker, MRI (magnetic resonance imag-ing) or CT (electronic computer X-ray tomography) contrast agent, or enzyme capable of producing a detectable product, radionuclide, biotoxin, cytokine (such as IL-2, etc.), anti-body, antibody Fc fragment, antibody scFv fragment, gold nanoparticle/nanorod, virus particle, liposome, nanomag-netic particle, prodrug activating enzyme (e.g., DT-diapho-rase (DTD) or biphenyl hydrolase-like protein (BPHL)), chemotherapeutic agent (e.g., cisplatin), or nanoparticle in any form.

In another preferred embodiment, the immunoconjugate contains: a multivalent (e.g., bivalent) VHH chain of the anti-VEGF single domain antibody according to the second aspect of the present invention, or the anti-VEGF single-domain antibody according to the third aspect of the present invention.

In another preferred embodiment, the multivalent means that the amino acid sequence of the immunoconjugate contains multiple repeats of the VHH chain of the anti-VEGF single-domain antibody according to the second aspect of the present invention, or the anti-VEGF single-domain antibody according to the third aspect of the present invention.

In the ninth aspect of the present invention, it provides a use of the VHH chain of the anti-VEGF single-domain antibody according to the second aspect of the present invention or the anti-VEGF single-domain antibody accord-ing to the third aspect for preparing (a) a medicine for inhibiting the angiogenesis;
(b) a medicine for treatment of diseases or disorders associated with VEGF.

In the tenth aspect of the present invention, it provides a pharmaceutical composition comprising:

(i) the complementarity determining region CDR of the anti-VEGF single-domain antibody VHH chain accord-ing to the first aspect of the present invention, the VHH chain of the anti-VEGF single-domain antibody according to the second aspect of the present invention, the anti-VEGF single-domain antibody according to the third aspect of the present invention or the immu-noconjugate according to the ninth aspect of the present invention; and
(ii) a pharmaceutically acceptable carrier.

In another preferred embodiment, the coupling moiety of the immunoconjugate is a drug, toxin, and/or therapeutic isotope.

In another preferred embodiment, the pharmaceutical composition further comprises another drug for the treat-ment of tumors, such as a cytotoxic drug.

In another preferred embodiment, the pharmaceutical composition is used to block the interaction between VEGFA and VEGFR2, or between VEGFA and VEGFR1.

In another preferred embodiment, the pharmaceutical composition is an injection formulation.

In another preferred embodiment, the pharmaceutical composition is used for preparing a medicine for treating a disease or disorder associated with VEGF, which comprises tumor or cancer or ocular sickness.

In another preferred embodiment, the tumor or cancer includes but is not limited to one or more of the following cancers: breast cancer, lung cancer, esophageal cancer, stomach cancer, colon cancer, thyroid cancer, nasopharyn-geal cancer.

In another preferred embodiment, the ocular sickness includes but is limited to age-related macular degeneration, diabetic retinopathy, retinal vein occlusion, pathological myopia, neovascular glaucoma, and other ophthalmic dis-eases involving neovascularization.

In the eleventh aspect of the present invention, it provides one or more uses of the anti-VEGF single domain antibody according to the third aspect of the present invention for preparing (a) a medicine for inhibiting the angiogenesis;
(b) a medicine for treatment of a disease or disorder associated with VEGF;
(c) for detection of human VEGF molecules;
(d) for flow cytometry detection;
(e) for cellular immunofluorescence detection;
(f) for treatment of a tumor;
(g) for tumor diagnosis.

In another preferred embodiment, the use is diagnostic and/or non-diagnostic, and/or therapeutic and/or non-thera-peutic.

In the twelfth aspect of the present invention, it provides an antibody including one or more VHH chains of the anti-VEGF single-domain antibody according to the second aspect of the present invention.

In another preferred embodiment, the antibody includes two VHH chains of the anti-VEGF single-domain antibody according to the second aspect of the present invention.

In another preferred embodiment, the antibody includes heavy chain variable region VHH according to the second aspect of the present invention.

In another preferred embodiment, the antibody can spe-cifically target VEGFA proteins with the correct spatial structure.

In another preferred embodiment, the antibody can rec-ognize human, mouse, rabbit and monkey VEGFA.

In another preferred embodiment, the antibody does not cross-react with human VEGFB, VEGFC, and VEGFD.

In another preferred embodiment, the antibody can block the interaction between VEGFA and VEGFR2, and between VEGFA and VEGFR1.

In another preferred embodiment, the antibody can inhibit neovascularization.

In another preferred embodiment, the antibody is single-domain antibody.

In the thirteenth aspect of the present invention, it pro-vides a recombinant protein, which comprises:

(i) the VHH chain according to the second aspect of the present invention, or the anti-VEGF single-domain antibody according to the third aspect of the present invention; and

(ii) an optional tag sequence to aid expression and/or purification.

In another preferred embodiment, the tag sequence comprises Fc tag, HA tag, and 6His tag.

In another preferred embodiment, the recombinant protein specifically binds to VEGF protein.

In the fourteenth aspect of the present invention, it provides a use of the VHH chain of the anti-VEGF single-domain antibody according to the second aspect of the present invention, the anti-VEGF single-domain antibody according to the third aspect of the present invention, or the immunoconjugate according to the eighth aspect of the present invention for preparation of a medicament, reagent, detection plate or kit;

wherein the reagent, detection plate or kit is used for detecting VEGF protein in the sample;

wherein the medicament is used for treating or preventing a disease or disorder associated with VEGF.

In another preferred embodiment, the detection includes flow cytometry detection and cellular immunofluorescence detection.

In another preferred embodiment, the disease or disorder comprises tumor or cancer or ocular sickness.

In another preferred embodiment, the tumor or cancer includes but is not limited to one or more of the following cancers: breast cancer, lung cancer, esophageal cancer, stomach cancer, colon cancer, thyroid cancer, nasopharyngeal cancer.

In another preferred embodiment, the ocular sickness includes but is not limited to age-related macular degeneration, diabetic retinopathy, retinal vein occlusion, pathological myopia, neovascular glaucoma, and other ophthalmic diseases involving neovascularization.

In the fifteenth aspect of the present invention, it provides a method for treating a disease, comprising administrating to a subject in need the single-domain antibody according to the third aspect of the present invention, or the immunoconjugate according to the eighth aspect of the present invention.

In another preferred embodiment, the subject includes a mammal, such as human, mouse, rabbit, monkey.

In the sixteenth aspect of the present invention, it provides a method for detecting VEGF protein in a sample, which comprises the steps of:

(1) contacting the sample with VHH chain according to the second aspect of the present invention or the immuneconjugate according to the eighth aspect of the present invention;

(2) detecting whether an antigen-antibody complex is formed, wherein the formation of the complex indicates the presence of VEGF protein in the sample.

In another preferred embodiment, the method is a non-diagnostic and non-therapeutic method.

In the seventeenth aspect of the present invention, it provides a VEGFA protein detection reagent, which comprises:

(i) the VHH chain according to the second aspect of the present invention, the single-domain antibody according to the third aspect of the present invention, or the immuneconjugate according to the eighth aspect of the present invention; and (ii) a detectologically acceptable carrier.

In another preferred embodiment, the coupling moiety of the immunoconjugate is a diagnostic isotope.

In another preferred embodiment, the detectologically acceptable carrier is nontoxic, inert aqueous carrier medium.

In another preferred embodiment, the detection reagent includes one or more reagents selected from the group consisting of isotope tracer, contrast agent, flow detection reagent, cell immunefluorescence detection reagent, nano-magnetic particle and imaging agent.

In another preferred embodiment, the detection reagent is used to detect in vivo.

In another preferred embodiment, the form of the detection reagent is liquid or powder (such as aqueous solution, injection, lyophilized powder, tablet, containing agent, inhalant).

In the eighteenth aspect of the present invention, it provides a kit to detect the VEGF protein, which comprises the immuneconjugate according to the eighth aspect of the present invention or the detection reagent according to the seventeenth aspect of the present invention.

In another preferred embodiment, the specification indicates that the kit is used to non-invasively detect VEGFA expression in the subject to be tested.

In the nineteenth aspect of the present invention, it provides a use of immunoconjugate according to the eighth aspect of the present invention for preparing the contrast agent to detect the VEGFA protein in vivo.

In another preferred embodiment, the detection is used for the diagnosis or prognosis of cancer.

In the twentieth aspect of the present invention, it provides framework regions or FRs of the VHH chain of the anti-VEGF single-domain antibody, wherein the framework regions (FRs) of the VHH chain consist of FR1 as shown in SEQ ID NO:4, FR2 as shown in SEQ ID NO: 5, FR3 as shown in SEQ ID NO: 6, and FR4 as shown in SEQ ID NO: 7; or FR1 as shown in SEQ ID NO: 10, FR2 as shown in SEQ ID NO: 11, FR3 as shown in SEQ ID NO: 12, and FR4 as shown in SEQ ID NO: 13.

In the twenty-first aspect of the present invention, it provides a method for treatment of a disease or disorder associated with VEGF by administrating the pharmaceutical composition of the tenth aspect of the present invention to a subject in need.

In another preferred embodiment, the subject includes a mammal, such as human.

It should be understood that, within the scope of the present invention, the technical features specifically described above and below (such as the Examples) can be combined with each other, thereby constituting a new or preferred technical solution which needs not be redundantly described one by one.

The results showed that the candidate antibody could block the interaction between human VEGFA and VEGF1 (IC$_{50\ hu\ bi-Nb24(Y)}$=0.168 ug/mL), and the blocking activity was superior to that of control antibody AVASTIN® (IC$_{50\ AVASTIN®}$=0.967 ug/mL).

Figure 11:
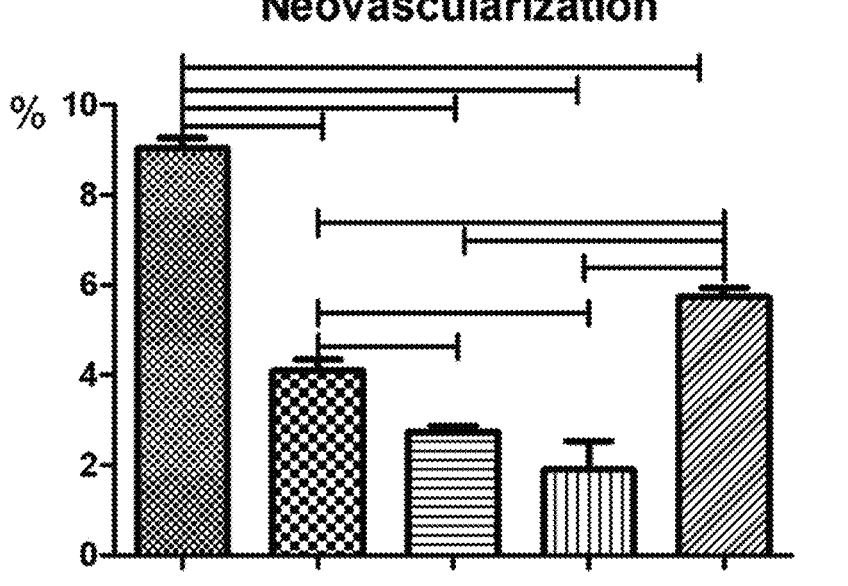

FIG. 11 shows the statistical results of the area of non-perfusion region of retina in OIR model mice. Mice were treated with different concentrations of humanized bivalent antibody expressed by yeast. The area of non-perfusion region of retina in experimental group was smaller than that in positive control group.

Figure 12:
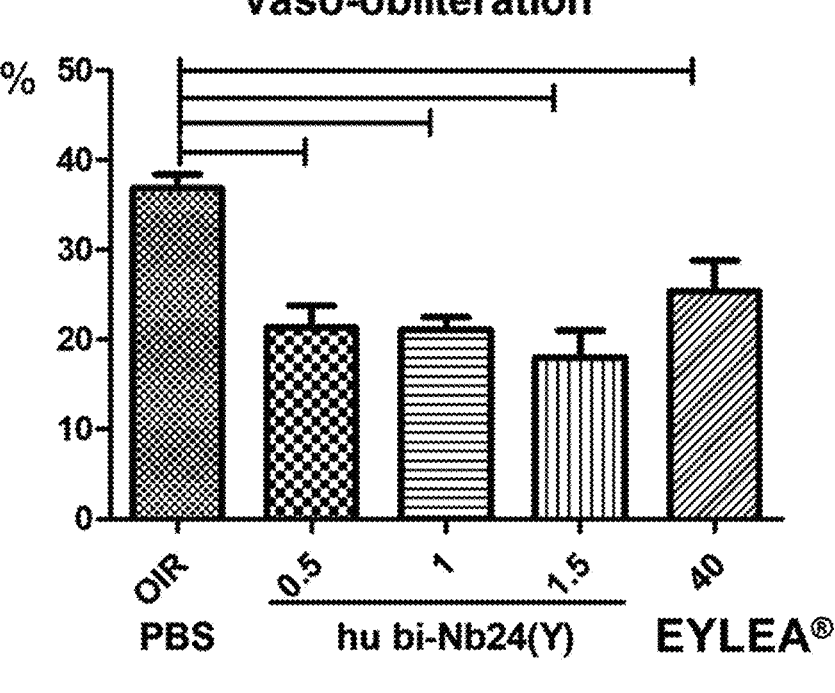

FIG. 12 shows the statistical results of retinal neovascularization clusters in OIR model mice. Compared with EYLEA® (positive control), humanized bivalent antibody expressed by yeast has more significant inhibitory effect on retinal neovascularization clusters at different concentrations, and the difference was statistically significant.

FIG. 13 shows the stability results of the candidate antibody detected by SEC-HPLC at different temperatures. FIG. 13A shows the stability results of the candidate antibody at 4° C. for 1 month. The results showed that the antibody exhibited good stability without obvious change at 4° C. for 1 month under non-preparation condition, showing better stability.

Figure 13A:
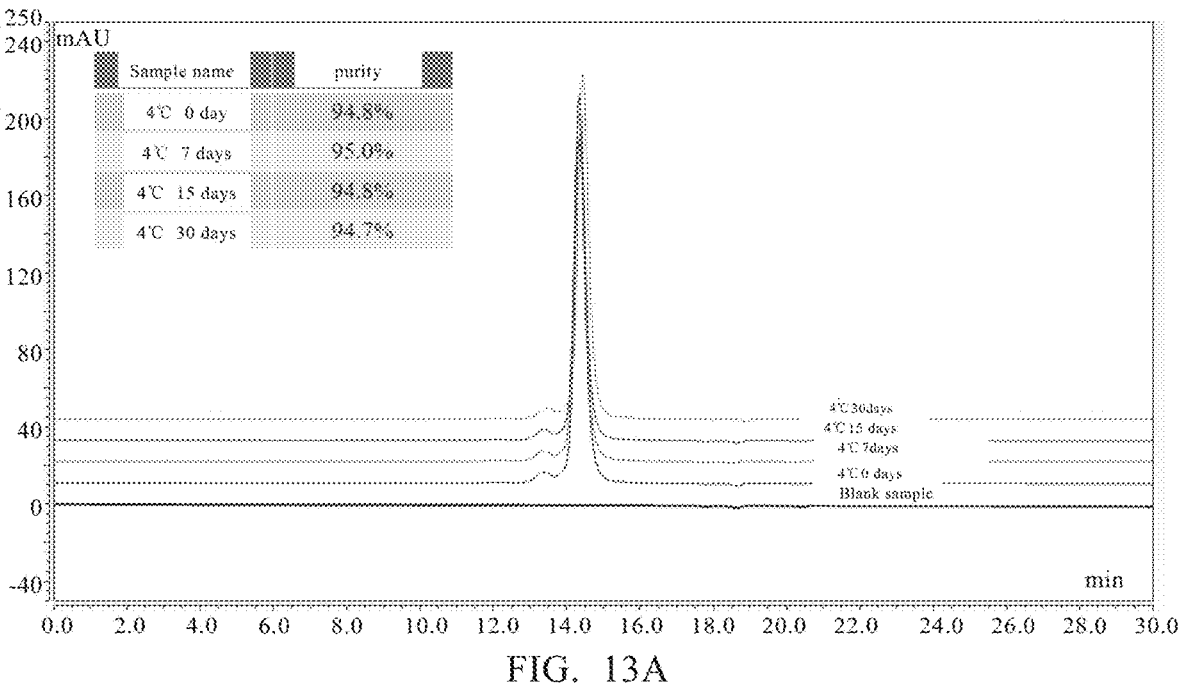
Figure 13B:
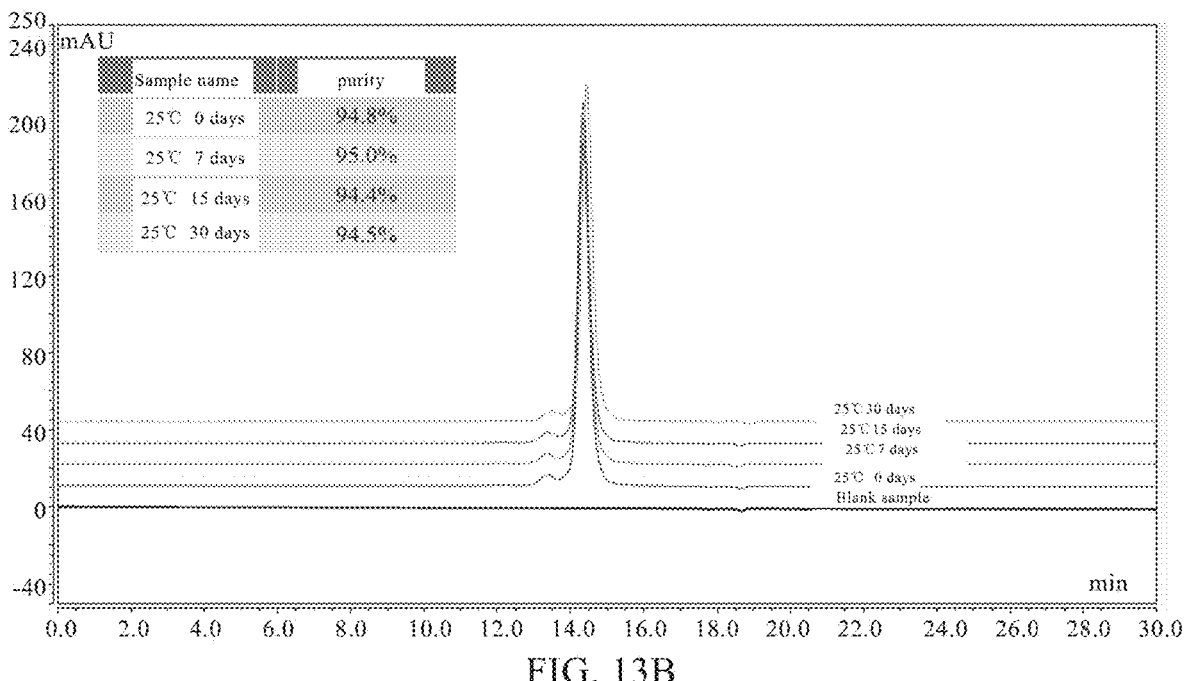
Figure 13C:
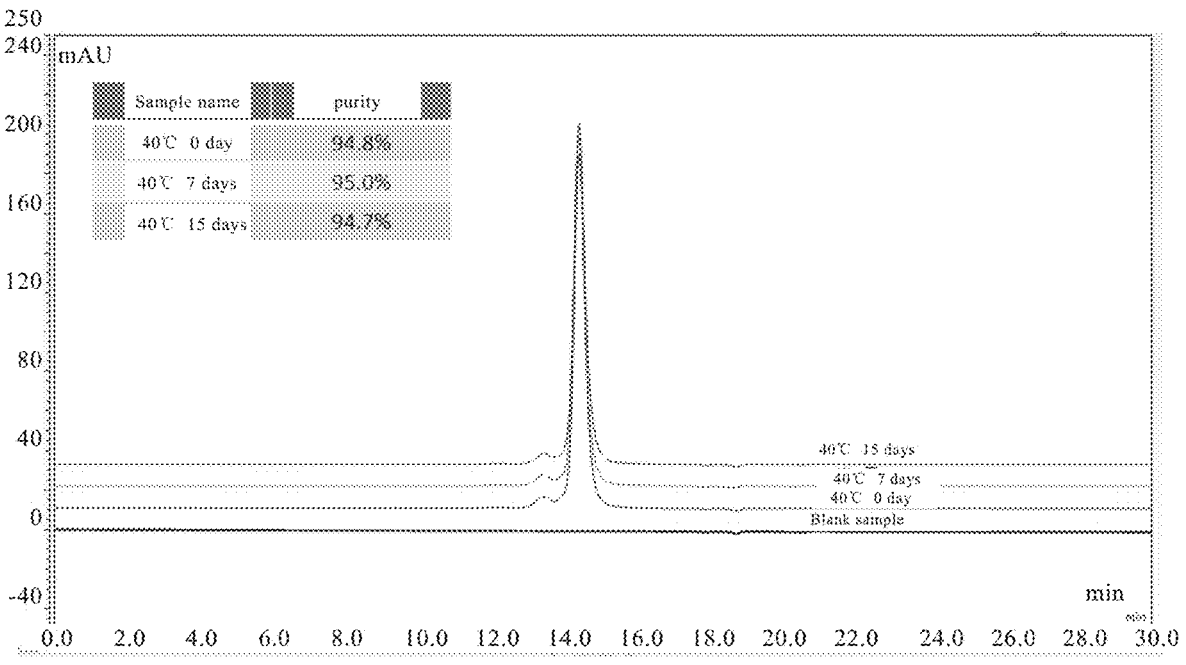
Figure 13D:
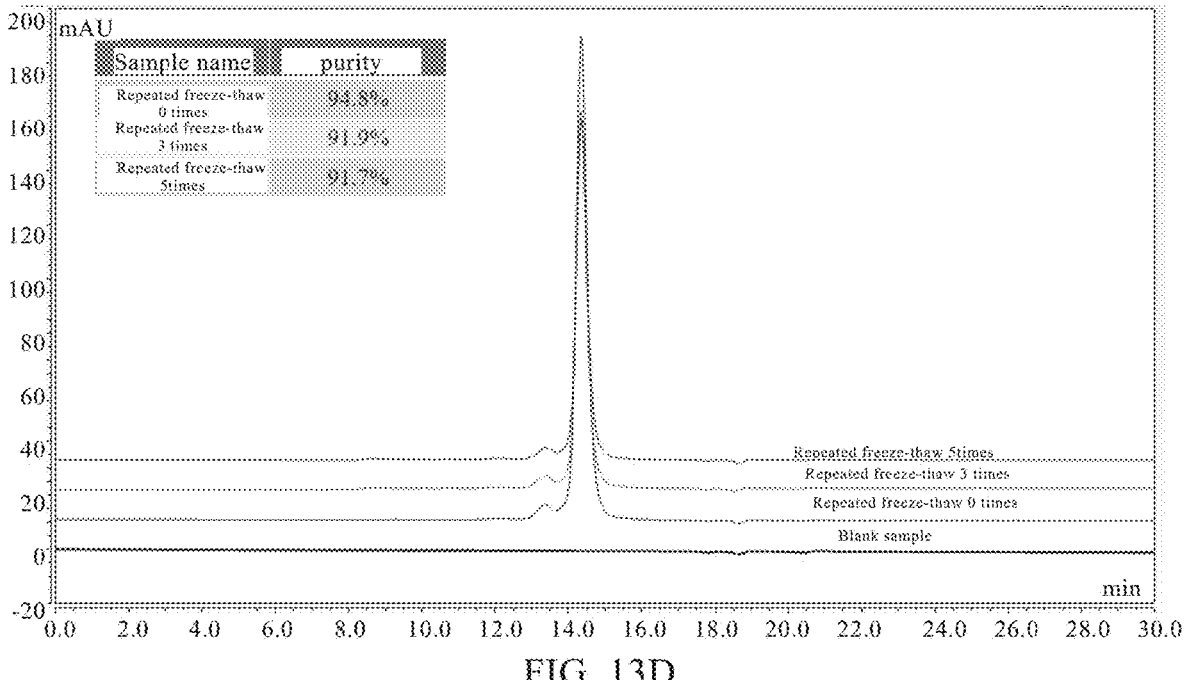

FIG. 13B shows the stability results of the candidate antibody at 25° C. for 1 month. The results showed that the antibody exhibited good stability without obvious change at 25° C. for 1 month under non-preparation condition, showing good stability. FIG. 13C shows the stability results of the candidate antibody at 40° C. for 15 days. The results showed that the antibody showed better stability without obvious change at 40° C. for 15 days under non-preparation condition, showing good stability. FIG. 13D shows the stability results of the candidate antibody after repeated freeze-thaw for 5 times at −20° C. The results showed that the antibody exhibited good stability without obvious purity change after repeated freeze-thaw for 5 times at −20° C. under non-preparation condition.

DETAILED DESCRIPTION OF INVENTION

After extensive and intensive researches and lots of screening, the present inventors have successfully obtained a class of anti-VEGF single-domain antibodies. The experimental results show that the single-domain antibody of the present invention can specifically recognize VEGFA, does not cross-react with VEGFB, VEGFC and VEGFD, and has good specificity. It can effectively block the interaction between VEGFA and VEGFR2, and between VEGFA and VEGFR1. It also has a good inhibitory effect on the neo-vascularization. The singe-domain antibody is easy to generate. Based on these, the invention is completed.

Specifically, the present inventors utilized human-derived VEGFA antigen protein to immunize camels to obtain a high-quality immune single-domain antibody gene library. Then the VEGF protein molecule was coupled to the enzyme labeled plate to display the correct spatial structure of the VEGF protein and was used as an antigen to screen the immune single domain antibody gene library (camel heavy chain antibody phage display gene library) via the phage display technology, thereby obtaining the VEGF specific single domain antibody gene. The gene was then transferred into mammalian cells to obtain a single domain antibody strain that could be efficiently expressed in mammalian cells and had high specificity. Thereafter, the anti-VEGF single-domain antibodies with blocking activity were identified by ELISA, flow cytometry and luciferase reporter gene detection system, etc.

Terms

As used herein, the terms "single-domain antibody of the present invention", "anti-VEGF single-domain antibody of the present invention", and "VEGF single domain antibody of the present invention" have the some meaning and can be used interchangeably, each refers to single domain antibodies that specifically recognize and bind to VEGFA (including human VEGFA). Preferably, the variable region of the single-domain antibody of the present invention has CDR1 as shown in SEQ ID NO: 1, CDR2 as shown in SEQ ID NO: 2, and CDR3 as shown in SEQ ID NO: 3. More preferably, the framework region of the single-domain antibody of the present invention has (a) FR1 as shown in SEQ ID NO: 4, FR2 as shown in SEQ ID NO: 5, FR3 as shown in SEQ ID NO: 6, and FR4 as shown in SEQ ID NO: 7; or (b) FR1 as shown in SEQ ID NO: 10, FR2 as shown in SEQ ID NO: 11, FR3 as shown in SEQ ID NO: 12, and FR4 as shown in SEQ ID NO: 13.

As used herein, the term "antibody" or "immunoglobulin" is a heterotetrameric glycoprotein of about 150,000 Daltons with the same structural characteristics, which consists of two identical light chains (L) and two identical heavy chains (H). Each light chain is connected to the heavy chain through a covalent disulfide bond, and the number of disulfide bonds between heavy chains of different immunoglobulin isotypes is different. Each heavy and light chain also has regularly spaced disulfide bonds in the chain. Each heavy chain has a variable region (VH) at one end, followed by multiple constant regions. Each light chain has a variable region (VL) at one end and a constant region at the other end. The constant region of the light chain is opposite to the first constant region of the heavy chain, and the variable region of the light chain is opposite to the variable region of the heavy chain. Special amino acid residues form an interface between the variable regions of the light chain and the heavy chain.

As used herein, the terms "single-domain antibody", "VHH", "NANOBODY®", "single-domain antibody" (single domain antibody, sdAb, or NANOBODY®) have the same meaning and can be used interchangeably, and refer to a single domain antibody (VHH) consisting of only one heavy chain variable region, which is the smallest antigen-binding fragment with complete functions wherein the VHH is constructed via cloning of the variable region of an antibody heavy chain. Usually, the antibody that naturally lacks the light chain and the heavy chain constant region 1 (CH1) is obtained, and then the variable region of the antibody heavy chain is cloned to construct a single domain antibody (VHH) consisting of only one heavy chain variable region.

As used herein, the term "variable" means that certain parts of the variable region in an antibody differ in sequence, which forms the binding and specificity of various specific antibodies for their specific antigens. However, the variability is not evenly distributed throughout the variable region of the antibody. It is concentrated in three segments called complementarity determining regions (CDRs) or hypervariable regions in the light chain variable regions and heavy chain variable regions. The more conserved part of the variable region is called the framework region (FR). The variable regions in the natural heavy and light chains each contain four FR regions, which are roughly in the R-fold configuration, connected by the three CDRs that form the connecting loop, and in some cases part of the P-folded structure may be formed. The CDRs in each chain are closely together through the FR region and together with the CDRs of the other chain to form the antigen-binding site of the antibody (see Kabat et al., NIH Publ. No. 91-3242, Volume I, pages 647-669) (1991)). The constant regions are not directly involved in the binding of antibodies to antigens, but they exhibit different effector functions, such as antibody-dependent cytotoxicity involved in antibodies.

As known to those skilled in the art, immunoconjugates and fusion expression products include: conjugates formed by combining drugs, toxins, cytokines, radionuclides, enzymes, and other diagnostic or therapeutic molecules with the antibodies or fragments thereof of the present invention. The present invention also includes cell surface markers or antigens that bind to the anti-VEGF protein antibody or fragments thereof.

As used herein, the terms "heavy chain variable region" and "VH" can be used interchangeably.

As used herein, the terms "determinant of variable region" and "complementarity determining region (CDR)" can be used interchangeably.

In a preferred embodiment of the present invention, the heavy chain variable region of the antibody includes three complementarity determining regions CDR1, CDR2, and CDR3.

In a preferred embodiment of the present invention, the heavy chain of the antibody includes the above heavy chain variable region and heavy chain constant region.

In the present invention, the terms "antibody of the present invention", "protein of the present invention", or "polypeptide of the present invention" can be used interchangeably, and refer to a polypeptide that specifically binds to the VEGF protein, such as a protein or polypeptide having a heavy chain variable region. They may or may not contain a starting methionine.

In general, the antigen-binding properties of antibodies can be described by three specific regions located in the variable region of the heavy chain, called variable regions (CDR). The segment is divided into 4 framework regions (FR), the amino acid sequences of the 4 FRs are relatively conservative, and do not directly participate in the binding reaction.

These CDRs form a circular structure, and the P-pleated sheet formed by the FRs in between are close to each other in space structure. The CDRs on the heavy chain and the CDRs on the corresponding light chain constitute the antigen binding site of the antibody. The amino acid sequences of antibodies of the same type can be compared to determine which amino acids constitute the FR or CDR regions.

The variable regions of the heavy chains of the antibodies of the present invention are of particular interest because at least part of them are involved in binding antigens. Therefore, the present invention includes those molecules having a CDR-containing antibody heavy chain variable region, as long as their CDRs have more than 90% (preferably more than 95%, most preferably more than 98%) homology with the CDRs identified herein.

The present invention includes not only whole antibodies, but also includes fragments, derivatives and analogs of the antibodies.

As used herein, the terms "fragment", "derivative" and "analog" refer to a polypeptide that substantially retains the same biological function or activity of the antibody of the present invention. The polypeptide fragment, derivative or analog of the present invention may be (i) a polypeptide having one or more conservative or non-conservative amino acid residues (preferably conservative amino acid residues) substituted, and such substituted amino acid residues may or may not be encoded by the genetic code, or (ii) a polypeptide with a substitution group in one or more amino acid residues, or (iii) a polypeptide formed by the fusion of a mature polypeptide with another compound (such as a compound that extends the half-life of the polypeptide, such as polyethylene glycol), or (iv) a polypeptide formed by fusing the additional amino acid sequence to the polypeptide sequence (such as a leader sequence or secretion sequence or a sequence or proprotein sequence used to purify the polypeptide, or a fusion protein formed with a 6His tag). According to the teachings herein, these fragments, derivatives and analogs are within the scope of those skilled in the art.

The antibody of the present invention refers to a polypeptide having VEGFA protein binding activity and containing the above-mentioned CDR regions. The term also includes variant forms of polypeptides containing the above CDR regions that have the same function as the antibodies of the present invention. These variant forms include (but are not limited to): one or more (usually 1-50, preferably 1-30, more preferably 1-20, most preferably 1-10) amino acid deletions, insertions and/or substitutions, and one or several (usually less than 20, preferably less than 10, and more preferably less than 5) amino acids addition to the C-terminal and/or N-terminal. For example, in the art, the substitution of amino acids with close or similar properties usually does not change the function of the protein. As another example, adding one or several amino acids to the C-terminus and/or N-terminus usually does not change the function of the protein. The term also includes active fragments and active derivatives of the antibodies of the present invention.

The variant forms of the polypeptide include: homologous sequences, conservative variants, allelic variants, natural mutants, induced mutants, proteins encoded by DNA that can hybridize with DNA encoding the antibody of the present invention under highly or lowly stringent conditions, and polypeptides or proteins obtained using antiserum against antibodies of the present invention.

The present invention also provides other polypeptides. In addition to almost full-length polypeptides, the present invention also includes fragments of single domain antibodies of the present invention. Generally, the fragment has at least about 50 consecutive amino acids, preferably at least about 50 consecutive amino acids, more preferably at least about 80 consecutive amino acids, and most preferably at least about 100 consecutive amino acids of the antibody of the present invention.

In the present invention, "conservative variant of the antibody of the present invention" refers to that compared with the amino acid sequence of the antibody of the present invention, at most 10, preferably at most 8, more preferably at most 5, and most preferably at most 3 amino acids are replaced by amino acids with similar or close properties to form a polypeptide. These conservative variant polypeptides are best produced by amino acid substitution according to Table 1.

TABLE 1

| The initial residues | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides polynucleotide molecules encoding the above antibodies or fragments thereof. The polynucleotide of the present invention may be in the form of DNA or RNA. DNA forms include cDNA, genomic DNA, or synthetic DNA. DNA can be single-stranded or double-stranded. DNA can be a coding strand or a non-coding strand.

The polynucleotide encoding the mature polypeptide of the present invention includes: a coding sequence encoding only the mature polypeptide; a coding sequence encoding the matnre polypeptide with various additional coding sequences; a coding sequence encoding the mature polypeptide (and optional additional coding sequences) and a non-coding sequence.

The term "polynucleotide encoding a polypeptide" may include a polynucleotide encoding the polypeptide, or a polynucleotide further containing additional coding and/or non-coding sequences.

The present invention also relates to polynucleotides that hybridize to the above-mentioned sequences and have at least 50%, preferably at least 70%, and more preferably at least 80% identity between the two sequences. The present invention particularly relates to polynucleotides that can hybridize to the polynucleotides of the present invention under stringent conditions. In the present invention, "stringent conditions" means: (1) hybridization and elution at lower ionic strength and higher temperature, such as 0.2× SSC, 0.1% SDS, 60° C.; or (2) denaturing agent, such as 50% (v/v) formamide, 0.1% calf serum/0.1% Ficoll, 42° C., etc. is added during hybridization; or (3) hybridization occurs only when the identity between the two sequences is at least 90%, and more preferably at least 95%. Furthermore, the polypeptide encoded by the hybridizable polynucleotide has the same biological function and activity as the mature polypeptide.

The full-length nucleotide sequence of the antibody of the present invention or a fragment thereof can generally be obtained by PCR amplification method, recombination method or artificial synthesis method. A feasible method is to use synthetic methods to synthesize the relevant sequences, especially when the fragment length is short. Generally, a fragment with a very long sequence can be obtained by synthesizing multiple small fragments and then connecting them. In addition, the coding sequence of the heavy chain and the expression tag (such as 6His) can also be fused together to form a fusion protein.

Once the relevant sequence is obtained, the relevant sequence can be obtained in large quantities by the recombination method. This is usually done by cloning it into a vector, then transferring it into a cell, and then isolating the relevant sequence from the propagated host cell by conventional methods. The biomolecules (nucleic acids, proteins, etc.) involved in the present invention include biomolecules that exist in an isolated form.

At present, the DNA sequence encoding the protein (or a fragment or a derivative thereof) of the present invention can be obtained completely by chemical synthesis. This DNA sequence can then be introduced into various existing DNA molecules (or vectors) and cells known in the art. In addition, mutations can also be introduced into the protein sequence of the present invention by chemical synthesis.

The present invention also relates to vectors containing the appropriate DNA sequence as described above and an appropriate promoter or control sequence. These vectors can be used to transform appropriate host cells so that they can express proteins.

The host cell may be a prokaryotic cell, such as a bacterial cell; or a lower eukaryotic cell, such as a yeast cell; or a higher eukaryotic cell, such as a mammalian cell. Representative examples are: *Escherichia coli, Streptomyces*; bacterial cells of *Salmonella typhimurium*; fungal cells such as yeast; insect cells of *Drosophila* S2 or Sf9; animal cells of CHO, COS7, 293 cells, etc.

Transformation of host cells with recombinant DNA can be performed using conventional techniques well known to those skilled in the art. When the host is a prokaryotic organism such as *E. coli*, competent cells that can absorb DNA can be harvested after the exponential growth phase and treated with the CaCl$_2$) method. The procedures used are well known in the art. Another method is to use MgCl$_2$. If necessary, transformation can also be carried out by electroporation. When the host is a eukaryote, the following DNA transfection methods can be used: calcium phosphate co-precipitation method, conventional mechanical methods such as microinjection, electroporation, liposome packaging, etc.

The obtained transformant can be cultured by a conventional method to express the polypeptide encoded by the gene of the present invention. Depending on the host cell used, the medium used in the culture can be selected from various conventional mediums. The cultivation is carried out under conditions suitable for the growth of host cells. When the host cell grows to an appropriate cell density, the selected promoter is induced by an appropriate method (such as temperature conversion or chemical induction), and the cell is cultured for a period of time.

The recombinant polypeptide in the above method may be expressed in a cell or on a cell membrane, or secreted out of the cell. If necessary, the recombinant protein can be isolated and purified by various separation methods using its physical, chemical and other characteristics. These methods are well known to those skilled in the art. Examples of these methods include, but are not limited to: conventional renaturation treatment, treatment with protein precipitation agent (salting out method), centrifugation, disruption of bacteria through penetration, ultra-treatment, ultra-centrifugation, molecular sieve chromatography (gel filtration), adsorption chromatography, ion exchange chromatography, high performance liquid chromatography (HPLC) and various other liquid chromatography techniques and combinations of these methods.

The antibody of the present invention may be used alone, or may be combined or coupled with a detectable label (for diagnostic purposes), a therapeutic agent, a PK (protein kinase) modified portion, or a combination or coupling of any of above these substances.

Detectable labels for diagnostic purposes include, but are not limited to: fluorescent or luminescent markers, radioactive markers, MRI (magnetic resonance imaging) or CT (electronic computer X-ray tomography) contrast agents, or an enzyme capable of producing a detectable product.

Therapeutic agents that can be combined or conjugated with the antibodies of the present invention include, but are not limited to: 1. radionuclides; 2. biotoxin; 3. cytokines such as IL-2, etc.; 4. gold nanoparticles/nanorods; 5. viruses particles; 6. liposomes; 7. magnetic nanosphere; 8. prodrug-activating enzymes (e.g., DT-diaphorase (DTD) or biphenylhydrolase-like protein (BPHL)); 10. chemtherapeutic agents (e.g., cis-platinum) or any form of nanoparticles, etc.

Vascular Endothelial Growth Factor (VEGF)

Vascular Endothelial Growth Factor (VEGF) is a highly specific growth factor promoting vascular endothelial cells. VEGF binds to its receptors on the endothelial cell membrane (vascular endothelial growth factor receptor or VEGFR) and cause the phosphorylation of the receptor, which activates the mitogen activated protein kinases (MAPK), to realize the mitogen properties and induce the endothelial cell proliferation. Due to its angiogenesis properties, VEGF can restore tissues oxygen supply when blood circulation is insufficient. When VEGF is overexpressed in tissues, it can lead to symptoms of diseases. For example, overexpression of VEGF can lead to vascular diseases in the retina, such as diabetic retinopathy. In addition, solid tumors cannot grow beyond a certain size limit without sufficient vascular supply to obtain the nutrients needed for growth. Therefore, in order to overcome this limitation, solid tumors express VEGF to facilitate their growth and metastasis.

VEGF family member includes VEGF-A, VEGF-B, VEGF-C, VEGF-D, VEGF-E, VEGF-F and Placenta Growth Factor (PGF). VEGF-A is most important factor that regulates the normal and pathological neovascularization (agiogenesis). The biological effect of VEGF-A is mediated by binding to specific receptors. The main binding specific receptors are vascular endothelial growth factor 1 (VEGFR-1) and vascular endothelial growth factor 2 (VEGFR-2). Among them, VEGFR-2 is considered to be the primary VEGFR, which plays an important role in vascular endothelial cell proliferation. VEGFR-2 enhances the cell mitosis by inducing VEGF to dimers and receptors that require auto-phosphorylation through intracellular kinases. VEGR-C and VEGF-D can regulate the formation of lymphatic vessels.

Pharmaceutical Composition

The present invention also provides a composition. Preferably, the composition is a pharmaceutical composition, which contains the above antibody or an active fragment thereof, and a pharmaceutically acceptable carrier. Generally, these substances can be formulated in a non-toxic, inert and pharmaceutically acceptable aqueous carrier medium, wherein the pH is usually about 5-8, preferably about 6-8, although the pH can vary depending on the nature of the substance being formulated and the condition to be treated. The formulated pharmaceutical composition can be administered by conventional routes, including (but not limited to): intratumoral, intraperitoneal, intravenous, or topical administration.

The pharmaceutical composition of the present invention can be directly used to bind VEGFA protein molecules, and thus can be used to treat tumors. In addition, other therapeutic agents can be used simultaneously.

The pharmaceutical composition of the present invention contains a safe and effective amount (such as 0.001-99 wt %, preferably 0.01-90 wt %, more preferably 0.1-80 wt %) of the above single domain antibody (or its conjugate) of the present invention and a pharmaceutical acceptable carrier or excipient. Such carriers include (but are not limited to): saline, buffer, glucose, water, glycerin, ethanol, and a combination thereof. The pharmaceutical preparation should match the mode of administration. The pharmaceutical composition of the present invention can be prepared in the form of an injection, for example, prepared by a conventional method using a physiological saline or an aqueous solution containing glucose and other adjuvants. Pharmaceutical compositions such as injections and solutions are preferably manufactured under sterile conditions. The amount of active ingredient administered is a therapeutically effective amount, for example, about 10 micrograms/kg body weight to about 50 mg/kg body weight per day. In addition, the polypeptide of the present invention can be used together with other therapeutic agents.

When using a pharmaceutical composition, a safe and effective amount of an immunoconjugate is administered to a mammal, wherein the safe and effective amount is usually at least about 10 g/kg body weight, and in most cases does not exceed about 50 mg/kg body weight, preferably the dose is about from 10 g/kg body weight to about 10 mg/kg body weight. Of course, the specific dosage should also consider factors such as the route of administration, the patient's health status, etc., which are within the skills of skilled physicians.

Anti-VEGF Single Domain Antibody

In the present invention, the anti-VEGF single domain antibody include monomer, bivalent antibody, and/or multivalent antibody.

In a preferred embodiment of the present invention, the anti-VEGF single domain antibody comprise one, two or more VHH chains of amino acid sequence as shown in SEQ ID NO: 8 and/or SEQ ID NO: 14.

Typically, the anti-VEGF single domain antibody comprises two VHH chains of amino acid sequence as shown in SEQ ID NO: 8 and/or SEQ ID NO: 14.

Typically, the anti-VEGF single domain antibody comprises VHH chains of amino acid sequence as shown in SEQ ID NO: 8 and/or SEQ ID NO: 14.

Typically, the anti-VEGF single domain antibody comprises two VHH chains of amino acid sequence as shown in SEQ ID NO: 14.

In a preferred embodiment of the present invention, the two VHH chains containing amino acid sequence as shown in SEQ ID NO: 8 are linked via a linker.

In a preferred embodiment of the present invention, the two VHH chains containing amino acid sequence as shown in SEQ ID NO: 14 are linked via linkers.

In a preferred embodiment of the present invention, the linker is selected from the following sequences: $(G_aS_b)_x$-$(G_mS_n)_y$, wherein each of a, b, m, n, x, and y is 0 or 1 or 1 or 2 or 3 or 4 or 5 or 6 or 7 or 8 or 9 or 10 (more preferably, a=4, while b=1, and m=3 while n=1).

In a preferred embodiment, the linker is selected from the group consisting of GGGGSGGGS (SEQ ID NO: 18), GS (SEQ ID NO: 19), GGGGS (SEQ ID NO: 20).

In a preferred embodiment, the amino acid sequence of the anti-VEGF antibody is shown as SEQ ID NO: 16.

In a preferred embodiment, the bivalent anti-VEGF antibody is hu bi-Nb24(Y).

Labeled Single-Domain Antibody

In a preferred embodiment of the present invention, the single-domain antibody has a detectable label. More preferably, the label is selected from the group consisting of: isotopes, colloidal gold labels, colored labels or fluorescent labels.

Colloidal gold labeling can be performed using methods known to those skilled in the art. In a preferred embodiment of the present invention, the anti-VEGF single-domain antibody is labeled with colloidal gold to obtain a colloidal gold labeled single-domain antibody.

The anti-VEGF single-domain antibody of the present invention has good specificity and high titer.

Detection Method

The present invention also relates to a method for detecting VEGF protein. The method steps are roughly as follows: obtaining a cell and/or tissue sample; dissolving the sample in a medium; and detecting the level of VEGF protein in the dissolved sample.

In the detection method of the present invention, the sample used is not particularly limited, and a representative example is a cell-containing sample present in a cell preservation solution.

Kit

The present invention also provides a kit containing the antibody (or a fragment thereof) or a detection plate of the present invention. In a preferred embodiment of the present invention, the kit further includes a container, an instruction for use, a buffer, and the like.

The present invention also provides a detection kit for detecting the level of VEGF, which includes an antibody that recognizes the VEGF protein, a lysis medium for dissolving the sample, general reagents and buffers required for the detection, such as various buffers, detection markers, detection substrates, etc. The detection kit may be an in vitro diagnostic device.

Application

As described above, the single-domain antibody of the present invention has a wide range of biological application value and clinical application value, and its application involves the diagnosis and treatment of VEGF-related diseases, basic medical research, biological research and other fields. A preferred application is for clinical diagnosis and targeted therapy for VEGF.

The main advantages of the present invention include:

(a) The single-domain antibody of the present invention is highly specific against VEGF protein with correct spatial structure.

(b) The single-domain antibody of the present invention can recognize the VEGF of human, mouse, rabbit, monkey.

(c) The single-domain antibody of the present invention only recognizes human VEGFA and does not cross-react with VEGFB, VEGFC and VEGFD, thus having good specificity.

(d) The single-domain antibody of the present invention can effectively block the interaction between VEGFA and VEGFR2, between VEGFA and VEGFR1, and the blocking activity is higher than that of the Aflibercept.

(e) The single-domain antibody of the present invention has a good inhibitory effect on the neovascularization, which is superior to that of the Aflibercept.

(f) The single-domain antibody of the present invention has good anti-tumor activity which is superior to that of the commercial product AVASTIN®.

(g) The production of the single-domain antibody of the present invention is simple.

(h) The single-domain antibody of the present invention has good stability under non-preparation condition.

The invention will be further illustrated with reference to the following specific examples. It is to be understood that these examples are only intended to illustrate the invention, but not to limit the scope of the invention. For the experimental methods in the following examples without particular conditions, they are performed under routine conditions (eg. Sambrook et al., Molecular Cloning: A Laboratory Manual (third edition) (2001, CSHL Press) or as instructed by the manufacturer. Unless otherwise specified, all percentages or parts are by weight.

Example 1: Screening and Expression of Anti-VEGF Single-Domain Antibody

In order to obtain a single-domain antibody specific for human VEGF, firstly, human VEGFA protein was transiently expressed by a mammalian cell HEK293F, and then used for immunization in a camel after affinity purification. For specific methods, please refer to the method described in Example 1 and Example 2 of the patent CN2018101517526. Briefly, two Xinjiang Bactrian camels were immunized with purified VEGFA protein. Total RNA was isolated from camel peripheral blood after 7 times of immunization. VHH gene was amplified by reverse transcription and PCR, and cloned into phage vector pMECS, and transformed into TG1 to construct phage display library. The constructed library sizes were $6.4 \times 10^8$ CFU and $5.5 \times 10^8$ CFU, and the insertion rates were 91.7% and 95.8%, respectively. Subsequently, the two libraries were screened by 6 and 5 rounds of screening, respectively to obtain enriched phages containing antibody genes. 300 clones were selected from each library for PE-ELISA identification, and the obtained positive clones were sequenced, and then the single-domain antibodies with different sequences were fused with Fc for expression, and the antibodies were transiently expressed by HEK293F system. The expression method was described in Example 3 of patent CN2018101517526.

Example 2: Screening of Blocking Type Anti-VEGF Single-Domain Antibody

Figure 1:
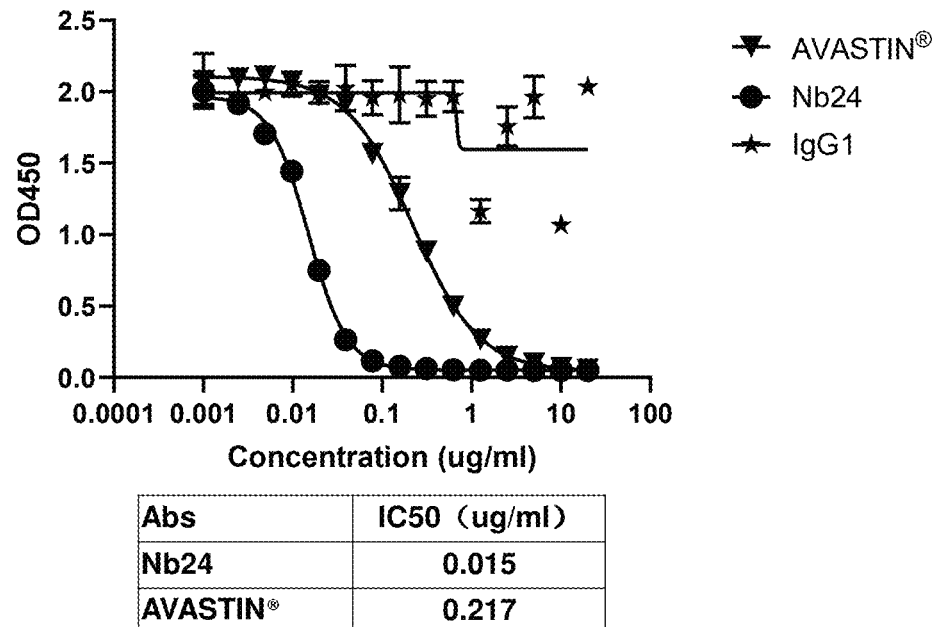
FIG. 1 shows the result of ELISA identification of a single-domain antibody that blocks the interaction between human VEGFA and VEGFR2. The blocking activity of the candidate antibody Nb24 was significantly better than that of the control antibody AVASTIN®, wherein AVASTIN® is Bevacizumab.

ELISA was used to screen the single-domain antibody that can block the interaction between human VEGFA and VEGFR2. (1) VEGFR2 protein was coated on an enzyme plate (1 ug/mL, 100 uL/well) and incubated at 4° C. overnight; (2) After washing with PBST for 5 times, 300 uL 1% BSA sealing solution was added and incubated at 37° C. for 2 hours; (3) After washing with PBST for 5 times, 50 uL gradient diluted antibody sample was added (two-fold gradient dilution starting from 40 ug/mL), and 50 uL 0.08 ug/mL biotinylated VEGFA protein was added into each well, and incubated at 37° C. for 1 hour. (4) After washing with PBST for 5 times, 100 uL SA-HRP (1:100000 dilution) was added and incubated at 37° C. for 1 hour. (5) After washing with PBST for 5 times, TMB chromochrome solution 100 uL was added, and developed at 37° C. for 10 min, 2M $H_2SO_4$ (50 uL/well) was added to terminate the reaction, and the absorption value was measured at 450 nm wavelength with a microplate reader. The results were shown in FIG. 1: the blocking activity of the Nb24 was superior to that of the control antibody (AVASTIN®) ($IC_{50\ Nb24}$=0.0149 ug/mL, $IC_{50\ AVASTIN®}$=0.2172 ug/mL).

Figure 2:
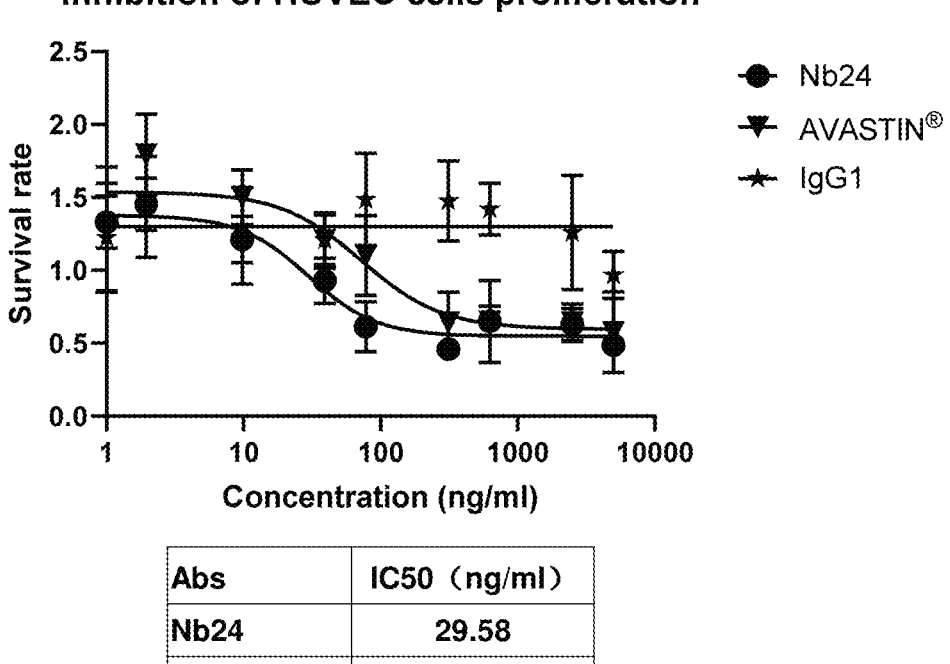
FIG. 2 shows the detection results of the inhibitory effect of candidate antibodies on HUVEC cell proliferation. The inhibitory effect of identified candidate antibody Nb24 on HUVEC cell proliferation was stronger than that of control antibody AVASTIN®.

Example 3: Expression and Purification of VEGF Single Domain Antibody in Eukaryotic Cell HEK293 and the Detection of the Blocking Function of Single Domain Antibody by Flow Cytometry Briefly, the method was as follows: (1) the well-grown HUVEC cells were digested with trypsin, neutralized in a complete medium, washed with PBS, and suspended at the concentration of $3 \times 10^4$/mL. Then the cells were divided into 96-well plates (100 uL/well) at 37° C., 5% $CO_2$, and cultivated for 20 h. (2) VEGFA was diluted to 100 ng/mL with DMEM of 2% FBS on the second day. The antibody was gradient diluted to 10000 ng/mL, 5000 ng/mL, 2500 ng/mL, 1250 ng/mL, 312.50 ng/mL, 78.13 ng/mL, 39.06 ng/mL, 9.77 ng/mL, 2 ng/mL. (3) Another 96-well plate was mixed with 60 uL VEGFA and the same volume of diluted antibody, and incubated at 37° C. for 2 h. Each mixture had three multiple wells. (4) The cell culture plate was taken out from the incubator, the supernatant was sucked, and the mixture of 100 ul from step (3) was added into the corresponding wells, respectively, and incubated at 37° C. for 72 h. (5) 72 h later, 10 ul/well CCK8 solution was added for 2 h color development. After color development, the absorbance value at OD450 wavelength was read with a microplate reader. The results were shown in FIG. 2: the inhibitory effect of the candidate antibody Nb24 on HUVEC cell was stronger than that of the control antibody AVASTIN® ($IC_{50\ Nb24}$=$^{29}$0.58 ng/mL, $IC_{50\ AVASTIN®}$=$^{72}$0.28 ng/mL).

Example 4: Humanization and Expression of Nb24 Domain Antibody

The candidate antibody was humanized wherein the variable region was kept unchanged, and humanized design was carried out for the sequence of the four framework regions. The transformation method refers to the method of Example 4 in patent application CN2018101517526. Then, the humanized antibody huNb24 sequence was constructed on pFUSE vector to fuse the humanized single-domain antibody with Fc sequence and expressed by HEK293F system. The expressed protein could be used for subsequent verification. The antibody sequences before and after humanization correspond to the following Table 2: Table 2

TABLE 2

| | Sequence numbering (SEQ ID NO:) | |
| --- | --- | --- |
| antibody region | Before humanization | After humanization |
| FR1 | 4 | 10 |
| CDR1 | 1 | 1 |
| FR2 | 5 | 11 |
| CDR2 | 2 | 2 |
| FR3 | 6 | 12 |
| CDR3 | 3 | 3 |
| FR4 | 7 | 13 |
| complete amino acid sequence | 8 | 14 |
| complete nucleotide sequence | 9 | 15 |

Example 5: Construction and Expression of Humanized Bivalent Antibody

Figure 3:
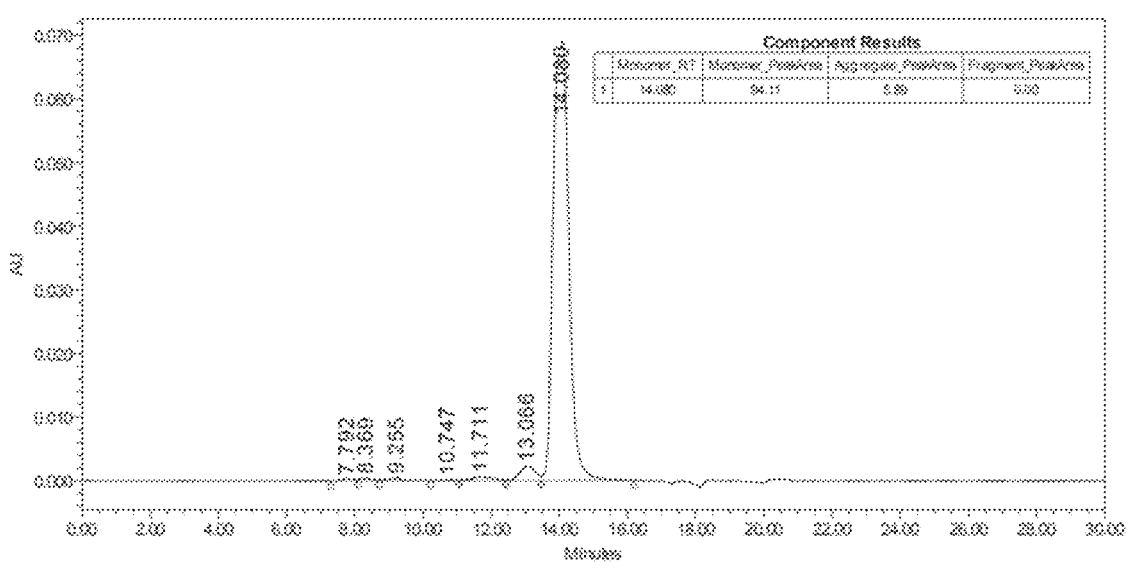
FIG. 3 shows the results of the SEC-HPLC detection of the huNb24 bivalent expressed by the yeast. The purified samples were identified by SEC-HPLC and the purity of the samples reached 94.11%.

The above humanized antibodies were constructed into a bivalent form and linked with the linker GGGGSGGGS (SEQ ID NO.18). After linking, the amino acid sequence was shown as SEQ ID NO: 16 (the corresponding coding nucleotide sequence was shown as SEQ ID NO: 17), and then expressed by *Pichia pastoris*. Briefly, the expression methods were as follows: (1) the single-domain antibody divalent sequence as shown in SEQ ID NO.16 was constructed into pPICZaA vector; (2) PpICZAA-Nb24-NB24 was linearized with SacI restriction enzyme and electrically transformed into X-33 competent cells; (3) The electro-transferred samples were coated on YPD flat medium with different concentrations of bleomycin resistance, and placed in a 30° C. incubator for 3-4 days. The specific implementation scheme was according to the pPICZaA vector instruction provided by Invitrogen company. (4) After monoclones were grown on the plate medium, monoclones were selected from plates with different concentrations and placed in BMGY medium. When the OD value of BMGY medium reached about 20, the bacteria were collected and replaced in BMMY medium for culture at 250 rpm at 28° C. (5) Thereafter, samples were taken every 24 hours, and methanol with a final volume of 1% was added and sampled. The sample was centrifuged at 12000 rpm for 5 minutes, then supernatant was taken and stored at −20° C. After continuous induction for 5 days, the cultivation was ended. (6) The samples were detected by SDS-PAGE and purified by ammonium sulfate precipitation. The results were shown in FIG. 3: the single-domain antibody bivalent antibody hu Bi-Nb24 (Y) obtained from the expressed supernatant was precipitated and purified by ammonium sulfate, and its purity was 94.11% detected by SEC-HPLC, which could be used for subsequent studies.

Figure 4:
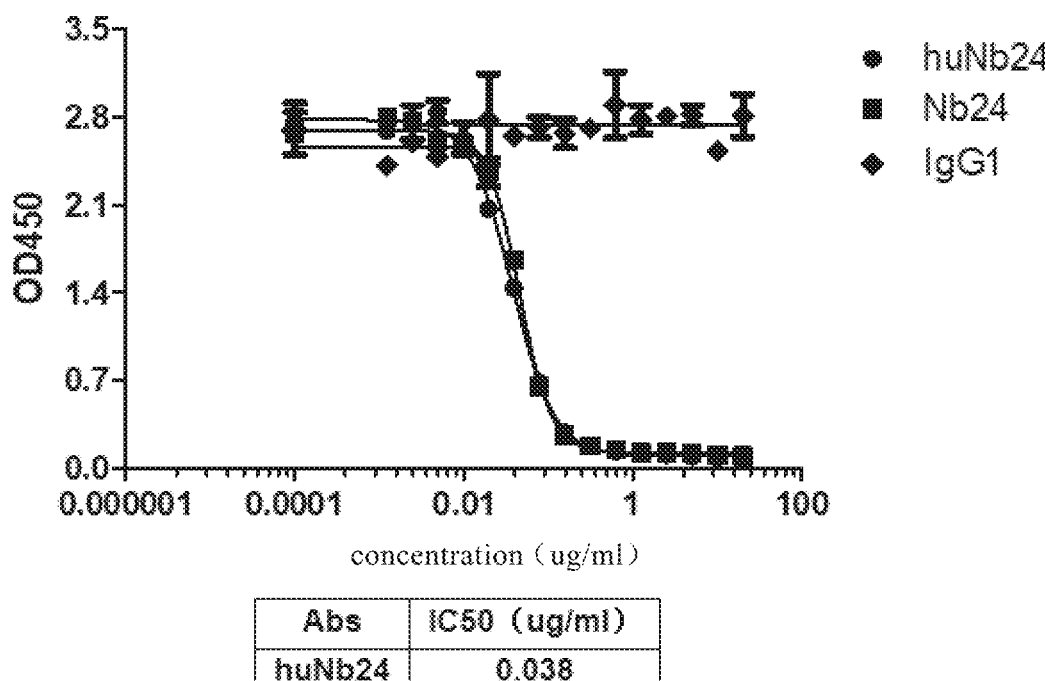
FIG. 4 shows the blocking activity of the humanized candidate antibody detected by ELISA. The results showed that the blocking activity of the antibody before humanization was similar to that after humanization (IC$_{50\ Nb}$24=0.045 ug/mL, IC$_{50\ huNb24}$=0.038 ug/mL), so that the humanization was successful. Nb24 was the antibody before humanization, and huNb24 was the antibody after humanization.
Figure 5:
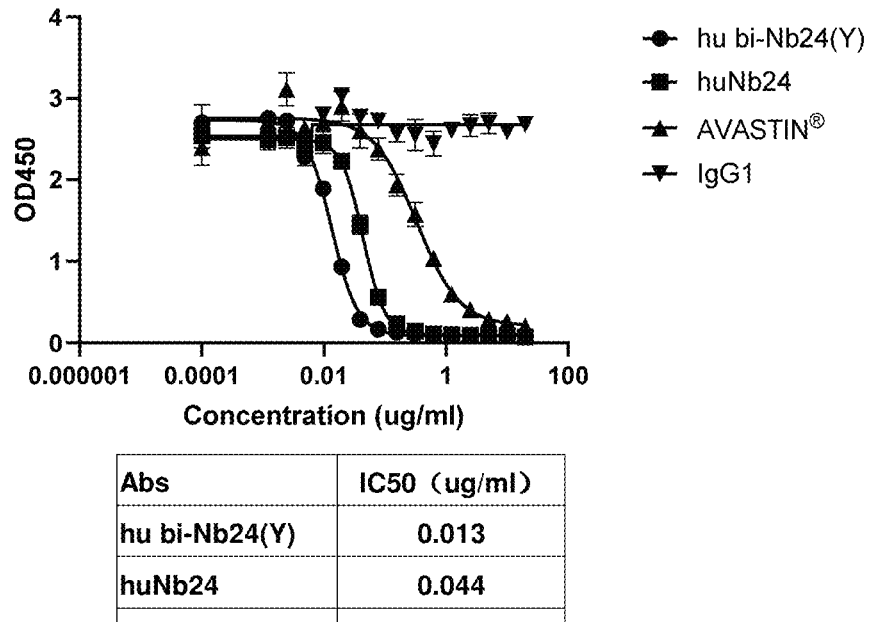
FIG. 5 shows the blocking activity of the humanized bivalent antibody expressed by the yeast via ELISA. The results showed that the blocking activity of the single-domain bivalent antibody expressed by the yeast was significantly improved (IC$_{50\ huNb24}$=0.044 ug/mL, IC$_{50hu\ bi-Nb24(Y)}$=0.013 ug/mL), and significantly higher than the blocking activity of the antibody AVASTIN®. The huNb24(Y) is humanized bivalent antibody expressed by the yeast.
Figure 6:
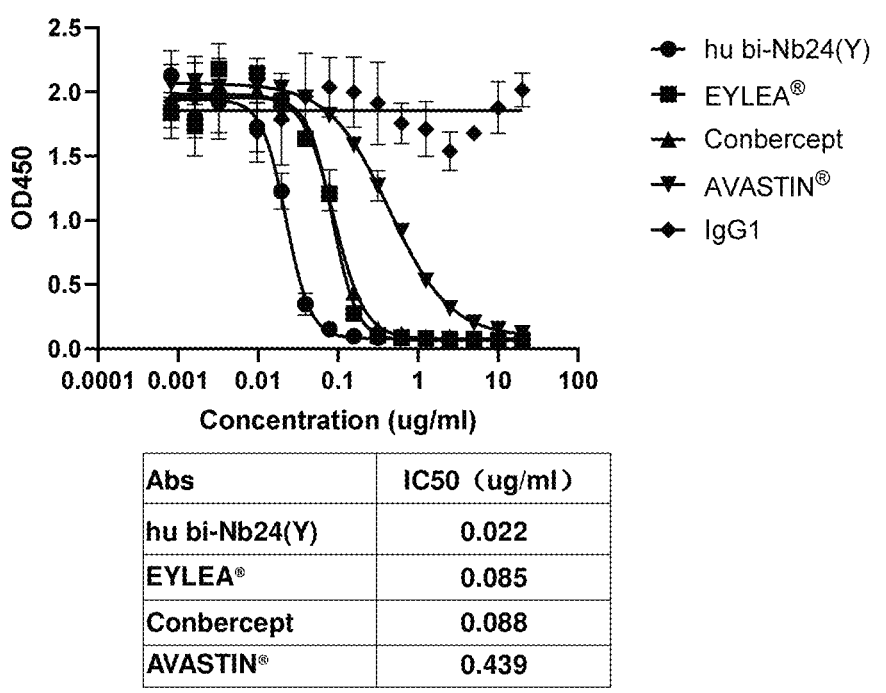
FIG. 6 compares the blocking activity of the humanized bivalent antibody and similar commercial products by ELISA. The results showed that the blocking activity of the humanized bivalent antibody expressed by the yeast had significant advantages, was superior to those of several commercial products (IC$_{50\ hu\ bi-Nb24(Y)}$=0.022 ug/mL, IC 50 EYLEA®=0.085 ug/mL, IC$_{50\ Conbercept}$=0.088 ug/mL, IC$_{50\ AVASTIN®}$=0.439 ug/mL). EYLEA® is Aflibercept and Conbercept is Conbercept antibody.

Example 6: Detection of Blocking Activity of Humanized Antibody and Bivalent Antibody Via ELISA The detection method was the same as that of Example 2, and the results were shown in FIG. 4. The blocking activity of humanized antibody was equivalent to that of antibody before humanization ($IC_{50}$Nb24=0.045 ug/mL, $IC_{50}$huNb24=0.038 ug/mL), indicating that the humanized transformation was successful. Then, the blocking activity of humanized single-domain antibody was compared with the divalent antibody expressed by yeast. The above experiments were repeated, and the results were shown in FIG. 5. The blocking activity of the bivalent single domain antibody hu Bi-Nb24 (Y) expressed by yeast increased by more than 3 times ($IC_{50}$huNb24=0.044 ug/mL, $IC_{50}$Hu Bi-Nb24 (Y)=0.013 ug/mL). The blocking activity was significantly higher than that of the control antibody AVASTIN® ($IC_{50\ AVASTIN®}$=0.331 ug/mL). Again, the above experimental method was used to detect and compare the blocking activity of the candidate antibody and similar commercial products, and the results were shown in FIG. 6. Humanized bivalent antibody hu Bi-Nb24 (Y) expressed by yeast showed superior blocking activity, $IC_{50}$HU Bi-NB24 (Y)=0.022 ug/mL, $IC_{50\ EYLEA®}$=0.085 ug/mL, $IC_{50\ Conbercept}$=0.088 ug/mL, $IC_{50\ AVASTIN®}$=0.439 ug/mL. These results indicate that the humanized bivalent antibody expressed by yeast has significantly superior blocking activity compared with the existing commercial products.

Figure 7:
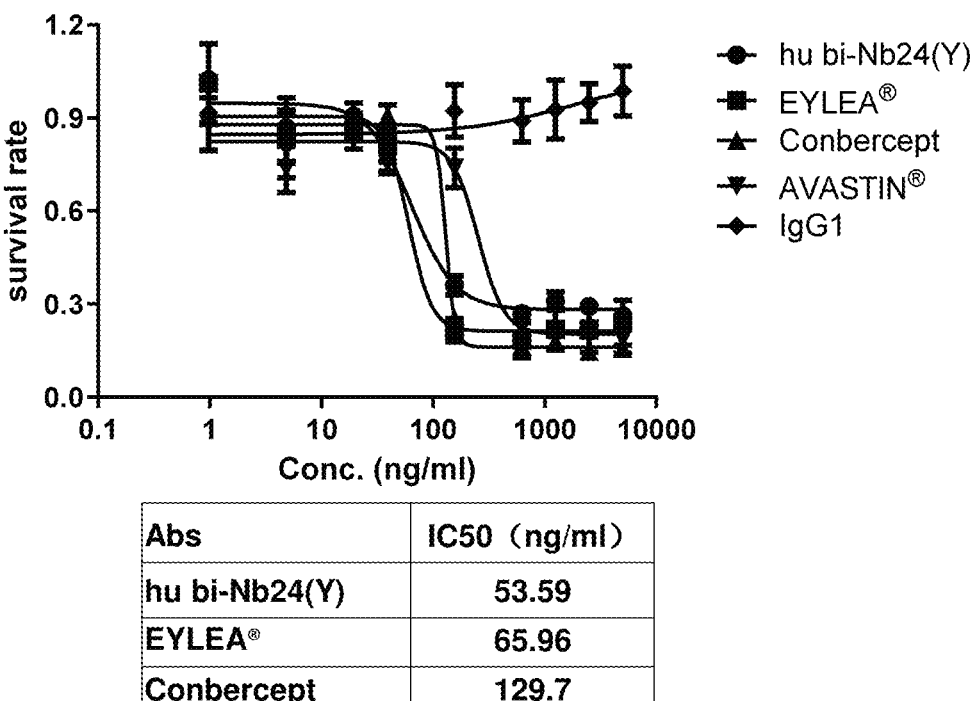
FIG. 7 shows the detection results of the inhibitory effect of the humanized bivalent antibody expressed by the yeast on HUVEC cell proliferation. The results showed that the effect of the humanized bivalent antibody expressed by the yeast was superior to those of similar commercial control products (IC$_{50\ hu\ bi-Nb24(Y)}$=53.59 ng/mL, IC$_{50\ EYLEA®}$=65.96 ng/mL, IC$_{50\ Conbercept}$=129.7 ng/mL, IC$_{50AVASTIN®}$=254.7 ng/mL).

Example 7: Inhibition Activity of Humanized Bivalent Antibody on HUVEC Proliferation The detection method was the same as that of Example 3, and the results were shown in FIG. 7: The human bivalent antibody hu Bi-Nb24 (Y) expressed by yeast had better inhibitory effect on HUVEC cell proliferation than similar commercial control products ($IC_{50\ HU\ Bi-NB24\ (Y)}$=53.59 ng/mL, $IC_{50\ EYLEA®}$=65.96 ng/mL, $IC_{50\ Conbercept}$=129.7 ng/mL, $IC_{50\ AVASTIN®}$=254.7 ng/mL).

Example 8: Specificity of Candidate Antibody Detected Via ELISA

Figure 8:
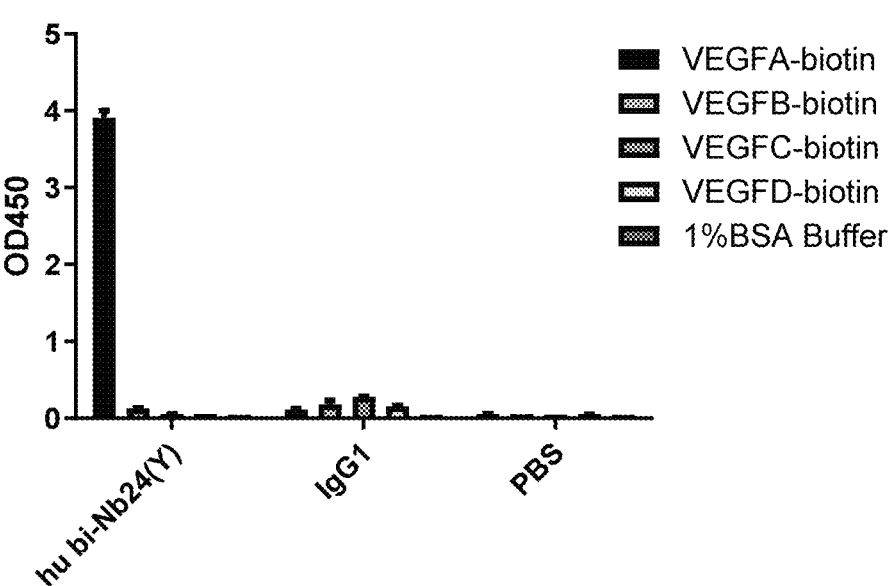
FIG. 8 shows the results of ELISA detection on whether the candidate antibody can cross-react with VEGF and its family proteins. The results showed that the humanized bivalent antibody with good specificity could cross-react with human VEGFA, but not with other proteins of the same family, such as VEGFB, VEGFC, VEGFD.

ELISA was used to verify whether the candidate antibodies could cross-react with VEGF homologous proteins. (1) 1 ug/mL antibody to be measured was added to the ELISA plate and coated overnight at 4° C. (100 uL/well); (2) After washing with PBST for 5 times, 300 uL 1% BSA was added into each well and seal for 2 hours at room temperature; (3) After washing with PBST for 5 times, 100 uL 1 ug/mL biotin-HVEGFA, Biotin-HVEGFB, Biotin-HVEGFC and Biotin-HVEGFD were added and incubated at 37° C. for 1 hour. (4) After washing with PBST for 5 times, 100 uL diluted SA-HRP (1:5000 diluted) was added at 37° C. and incubated for 1 hour; (5) After washing with PBST for 5 times, TMB solution (100 uL) was added and developed at 37° C. for 10 min, add 2M $H_2SO_4$ (50 uL/well) was added to terminate the reaction, and the absorption value at 450 nm wavelength was measured with a microplate reader. Results were shown in FIG. 8. Humanized bivalent antibody HU Bi-Nb24 (Y) could react with human VEGFA, but did not cross-react with other proteins in the same family such as VEGFB, VEGFC, and VEGFD.

Figure 9:
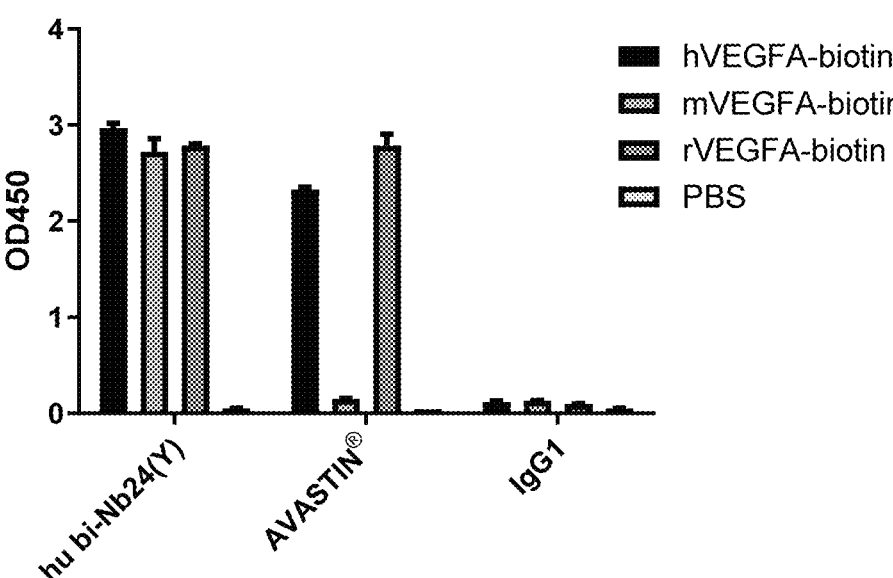
FIG. 9 shows the results of ELISA detection on whether the candidate antibody can cross-react with VEGF from other species. The results showed that humanized bivalent antibody could recognize the VEGFA of any of human, mouse, rabbit.

Similarly, ELISA was used to determine whether the candidate antibodies could cross-react with other species of VEGF. (1) 1 ug/mL antibody to be measured was added to the ELISA plate and coated overnight at 4° C. with 100 uL/well; (2) After washing with PBST for 5 times, 300 uL 1% BSA was added into each well and seal for 2 hours at room temperature; (3) After washing with PBST for 5 times, 100 uL 1 ug/mL biotin-HVEGFA (human), Biotin-MVEGFA (mouse) and Biotin-RVEGFA (rabbit) were added and incubated at 37° C. for 1 hour. (4) After washing with PBST for 5 times, 100 uL diluted SA-HRP (1:5000 diluted) was added at 37° C. and incubate for 1 hour; (5) After washing with PBST for 5 times, TMB solution (100 uL) was added and developed at 37° C. for 10 min, add 2M $H_2SO_4$ (50 uL/well) was added to terminate the reaction, and the absorption value at 450 nm wavelength was measured with a microplate reader. Results were shown in FIG. 9, humanized bivalent antibody hu bi-Nb24 (Y) could recognize human, rat and rabbit VEGFA. In addition, since the corresponding sequence of human VEGF121 was identical to that of cynomolgus monkey, it is suggested that the candidate antibody could also recognize VEGFA of cynomolgus monkey.

Figure 10:
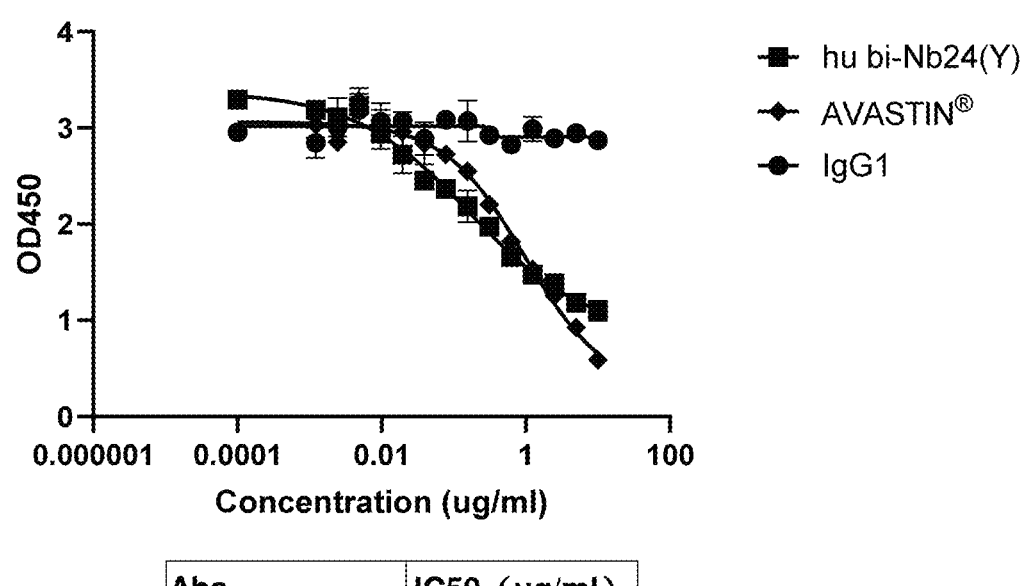
FIG. 10 shows the results of ELISA detection that the interaction between human VEGFA and VEGF1 is blocked by the humanized bivalent antibody expressed by the yeast.

Example 9: ELISA Detection of Blocking Activity of Humanized Bivalent Antibody on VEGFR1/VEGFA Interaction (1) VEGFR1 protein was coated on an enzyme plate (1 ug/mL, 100 uL/well) and incubated at 4° C. overnight. (2) After washing with PBST for 5 times, 300 uL 1% BSA sealing solution was added and incubated at 37° C. for 2 hours; (3) After washing with PBST for 5 times, 50 uL gradient diluted antibody sample was added (two-fold gradient dilution starting from 20 ug/mL), and 50 uL 0.08 ug/mL biotinylated VEGFA protein was added into each well, and incubated at 37° C. for 1 hour. (4) After washing with PBST for 5 times, 100 uL SA-HRP (1:100000 dilution) was added and incubated at 37° C. for 1 hour. (5) After washing with PBST for 5 times, TMB solution (100 uL) was added and developed at 37° C. for 10 min, 2M $H_2SO_4$ (50 uL/well) was added to terminate the reaction, and the absorption value at 450 nm wavelength was measured with a microplate reader. The results were shown in FIG. 10: The candidate antibody hu bi-Nb24(Y) could block the interaction between human VGEFA and VEGFR1 ($IC_{50\ hu\ bi-Nb24\ (Y)}$=0.168 ug/mL), and its blocking activity was superior to that of control antibody AVASTIN® ($IC_{50\ AVASTIN®}$=0.967 ug/mL).

Example 10: Inhibitory Activity of Candidate Antibody on Intraocular Vascular Growth in Neonatal Mouse OIR Model (1) OIR model, a classical mouse model for studying neovascularization, was adopted. The 7-day-old male C57BL/6J mice were reared in a closed container with 75% oxygen concentration until 12 days, during which the oxygen concentration in the oxygen chamber was regularly monitored to maintain at 75%, and then they were moved to a normal air environment for 5 days. P7 (7 days of age) to P12 (12 days of age) corresponds to the stage of retinal vascular occlusion, P12 to P17 (17 days of age) corresponds to the stage of hypoxia and abnormal vascular proliferation, and P17 to P21 (21 days of age) corresponds to the recovery stage of abnormal vascular proliferation. P17 was used as the observation point for abnormal neovascularization. Vitreous injection of luL hu bi-Nb24 (Y) with different concentrations (1.5 mg/mL, 1.0 mg/mL, 0.5 mg/mL) and control antibody EYLEA® at 40 mg/mL was performed in mice of OIR model group at P12. The mice were then moved to normal air and fed to P17.

(2) FitC-IB4 staining of retinal vascular endothelial cells was used for retinal placement, and abnormal neovascularization clusters and non-perfusion areas of the retina were observed at P17 in OIR model. The eyeballs of C57BL/6J mice were removed immediately after the mice were executed, fixed in 4% paraformaldehyde for 1 to 2 hrs. Under the operating microscope, the wall along the limbus of the corneal was cut, the lens and vitreous were removed, and the cortex on retinal nerve fiber layer and pigment were separated. The sclera, choroid and retinal pigment in the cortex were removed, the retinal nerve fiber layer was rinsed in PBS, and the residual vitreous body was removed. The cells were blocked with PBS containing 1 mg/mL BSA and 0.3% TX-100 for 1-2 h. The fitC-IB4 solution (diluted at 1:50) was added, and incubated at 4° C. for 48 h. After removal, the retinal nerve fiber layer was washed with PBS for 15 min (3 times). The retinal nerve fiber layer was spread upward on the slide, radially cut with the optic nipple as the center, and the tablet was sealed, observed and photographed under fluorescence microscope and confocal microscope.

Results were shown in FIGS. 11 and 12. In FIG. 11, compared with OIR negative control group, hu bi-Nb24(Y) at three concentrations (1.5 mg/mL, 1.0 mg/mL and 0.5 mg/mL) could reduce the area of non-perfusion area of retina, with statistical significance ($P<0.05$). The positive control drug, EYLEA® (40 mg/mL), also reduced the area of the non-perfusion area of the retina. The non-perfusion area of retina of hu bi-Nb24 (Y) at three concentrations (1.5 mg/mL, 1.0 mg/mL and 0.5 mg/mL) was smaller than that of EYLEA®, but there was no statistical difference. In FIG. 12, as compared with OIR, hu bi-Nb24 (Y) at three concentrations (1.5 mg/mL, 1.0 mg/mL, 0.5 mg/mL) and EYLEA® reduced angiogenesis clusters with statistical significance. Compared with EYLEA®, hu bi-Nb24(Y) at three concentrations (1.5 mg/mL, 1.0 mg/mL, 0.5 mg/mL) had a smaller percentage of retinal neovascularization clusters, and the difference was statistically significant. With the increase of hu bi-Nb24(Y) concentration, the percentage of retinal neovascular clusters decreased at P17 (0.5 VS 1, $P=0.0027$; 0.5 vs 1.5, $P=0.0177$; 1 vs 1.5, $P=0.2417$).

Example 11: Stability Study of Candidate Antibody

Candidate antibody hu bi-nb24 (Y) with a concentration of 1 mg/mL was placed in 10 mM PB solution at −20° C. (repeated freeze-thaw), 4° C., 25° C. and 40° C., respectively, and samples were taken at different time points for SEC-HPLC detection. The Adcance Bio SEC 130A 2.7 um 7.8*300 mm column was used, the detection wavelength was 280 nm, the speed was 0.5 mL/min at room temperature, and the flow was equably elution with 200 mM pH7.0 PB solution for 30 min.

The detection results were shown in FIG. 13. The purity of the candidate antibody did not change significantly when it was placed at 4° C. for 1 month (FIG. 13A), 25° C. for 1 month (FIG. 13B), 40° C. for 15 days (FIG. 13C), and −20° C. for 5 times (FIG. 13D), indicating that the antibody had good stability under non-preparation conditions.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

Sequence information of the present invention:

```
                                              SEQ ID NO. 1
GFTFDDPDVG

SEQ ID NO. 2
ISKDGST

SEQ ID NO. 3
AADSNPIAPIRTCLGWYNY

SEQ ID NO. 4
QVQLQESGGGSVQAGGSLRLSCTAS

SEQ ID NO. 5
WFRQAPGNECELVST

SEQ ID NO. 6
YYTDSVKGRFTISQDYAKNTVYLQMNSLKPEDTAVYYC

SEQ ID NO. 7
WGQGTQVTVSS

SEQ ID NO. 8
QVQLQESGGGSVQAGGSLRLSCTASGFTFDDPDVGWFRQAPGNECELVST

ISKDGSTYYTDSVKGRFTISQDYAKNTVYLQMNSLKPEDTAVYYCAADSN

PIAPIRTCLGWYNYWGQGTQVTVSS

SEQ ID NO. 9
CAGGTGCAGCTGCAGGAGTCTGGAGGAGGCTCGGTGCAGGCTGGAGGGTC

TCTGAGACTCTCCTGTACAGCCTCTGGATTCACTTTTGATGATCCTGACG

TGGGCTGGTTCCGCCAGGCTCCAGGGAATGAGTGCGAGTTGGTCTCAACT

ATTAGTAAGGATGGTAGTACATACTATACAGACTCCGTGAAGGGCCGATT

CACCATCTCCCAAGACTACGCCAAGAACACGGTGTATCTGCAAATGAACA

GCCTGAAACCTGAGGACACGGCCGTGTATTACTGTGCGGCAGACTCCAAT

CCTATAGCGCCTATTAGAACTTGTTTGGGGTGGTATAACTACTGGGGCCA

GGGGACCCAGGTCACCGTCTCCTCAGC

SEQ ID NO. 10
EVQLQESGGGLVQPGGSLRLSCTAS

SEQ ID NO. 11
WFRQAPGNECELVST

SEQ ID NO. 12
YYTDSVKGRFTISRDYAKNTVYLQMNSLRAEDTAVYYC

SEQ ID NO. 13
WGQGTLVTVSS

SEQ ID NO. 14
EVQLQESGGGLVQPGGSLRLSCTASGFTFDDPDVGWFRQAPGNECELVST

ISKDGSTYYTDSVKGRFTISRDYAKNTVYLQMNSLRAEDTAVYYCAADSN

PIAPIRTCLGWYNYWGQGTLVTVSS

SEQ ID NO. 15
GAGGTGCAGCTGCAGGAGAGCGGCGGCGGCCTGGTGCAGCCCGGCGGCAG

CCTGAGGCTGAGCTGCACCGCCAGCGGCTTCACCTTCGACGACCCCGACG

TGGGCTGGTTCAGGCAGGCCCCCGGCAACGAGTGCGAGCTGGTGAGCACC

ATCAGCAAGGACGGCAGCACCTACTACACCGACAGCGTGAAGGGCAGGTT

CACCATCAGCAGGGACTACGCCAAGAACACCGTGTACCTGCAGATGAACA
```

-continued

GCCTGAGGGCCGAGGACACCGCCGTGTACTACTGCGCCGCCGACAGCAAC

CCCATCGCCCCCATCAGGACCTGCCTGGGCTGGTACAACTACTGGGGCCA

GGGCACCCTGGTGACCGTGAGCAGC

SEQ ID NO. 16

EVQLQESGGGLVQPGGSLRLSCTASGFTFDDPDVGWFRQAPGNECELVST

ISKDGSTYYTDSVKGRFTISRDYAKNTVYLQMNSLRAEDTAVYYCAADSN

PIAPIRTCLGWYNYWGQGTLVTVSSGGGGSGGGSEVQLQESGGGLVQPGG

SLRLSCTASGFTFDDPDVGWFRQAPGNECELVSTISKDGSTYYTDSVKGR

FTISRDYAKNTVYLQMNSLRAEDTAVYYCAADSNPIAPIRTCLGWYNYWG

QGTLVTVSS

SEQ ID NO. 17

GAAGTTCAACTTCAAGAGTCTGGTGGTGGTTTAGTTCAACCAGGTGGGTC

TTTGAGATTGTCTTGTACTGCTTCTGGTTTTACTTTTGATGATCCAGATG

TTGGTTGGTTTAGACAAGCTCCAGGTAATGAATGTGAATTAGTTTCTACT

ATTTCTAAGGATGGTTCTACTTACTACACTGACTCTGTTAAGGGTAGATT

CACTATTTCCAGAGATTACGCTAAGAACACTGTTTACTTGCAAATGAACT

-continued

CTTTGAGAGCTGAAGATACTGCTGTTTACTACTGTGCTGCTGATTCCAAT

CCAATTGCTCCAATTAGAACTTGTTTGGGATGGTACAACTACTGGGGTCA

AGGTACTTTGGTTACTGTTTCTTCTGGTGGTGGAGGTTCTGGAGGTGGTT

CTGAAGTTCAATTGCAAGAATCTGGTGGTGGTTTGGTTCAACCAGGTGGT

TCTTTGAGATTGTCTTGTACTGCTTCTGGATTCACTTTTGATGATCCAGA

TGTTGGTTGGTTTAGACAAGCTCCAGGTAATGAATGTGAATTGGTTTCTA

CTATTTCTAAGGATGGTAGTACTTACTACACTGATTCTGTTAAGGGTAGG

TTTACTATTTCCAGAGATTACGCAAAGAACACCGTCTACTTGCAAATGAA

CTCTTTGAGAGCTGAGGATACTGCTGTCTACTACTGTGCTGCTGATTCCA

ACCCAATCGCTCCAATCAGAACCTGTTTGGGTTGGTACAACTACTGGGGT

CAAGGTACTTTGGTCACTGTTTCCTCT

SEQ ID NO. 18
GGGGSGGGS

SEQ ID NO. 19
GS

SEQ ID NO. 20
GGGGS

---

The invention claimed is:

1. An anti-VEGF single-domain antibody, which has a VHH chain having the amino acid sequence of SEQ ID NO: 8 or 14;
   wherein the single-domain antibody specifically recognizes VEGFA.

2. The anti-VEGF single-domain antibody of claim 1, wherein the single-domain antibody comprises monomer, bivalent antibody and/or multivalent antibody.

3. The anti-VEGF single-domain antibody of claim 1, wherein the single-domain antibody has a VHH chain having the amino acid sequence of SEQ ID NO: 14.

4. The anti-VEGF single-domain antibody of claim 1, wherein the single-domain antibody is a humanized antibody.

5. The anti-VEGF single-domain antibody of claim 1, wherein the anti-VEGF antibody comprises two VHH chains having the amino acid sequences of SEQ ID NO: 8 or SEQ ID NO: 14.

6. The anti-VEGF single-domain antibody of claim 5, wherein the two VHH chains have the amino acid sequences of SEQ ID NO: 8 or 14 are linked via a linker.

7. The anti-VEGF single-domain antibody of claim 6, wherein the linker is selected from the group consisting of GGGGSGGGS (SEQ ID NO: 18), GS (SEQ ID NO: 19), and GGGGS (SEQ ID NO: 20).

8. The anti-VEGF single-domain antibody of claim 1, wherein the anti-VEGF single-domain antibody has the amino acid sequence of SEQ ID NO: 16.

9. An immunoconjugate containing:
   (a) an anti-VEGF single-domain antibody of claim 1, and
   (b) a coupling moiety selected from the group consisting of: a detectable label, drug, toxin, cytokine, radionuclide, enzyme, gold nanoparticles/nanorods, magnetic nanoparticles, viral coat proteins, and a combination thereof.

10. A kit comprising an anti-VEGF single-domain antibody of claim 1 or a conjugate thereof, and an instruction for use.

11. A pharmaceutical composition which comprises an anti-VEGF single-domain antibody of claim 1 and one or more pharmaceutically acceptable carriers.

12. A method for detecting VEGF protein in a sample, which comprises the steps of:
   (1) contacting the sample with the anti-VEGF single-domain antibody of claim 1;
   (2) detecting whether an antigen-antibody complex is formed, wherein the formation of the complex indicates the presence of VEGF protein in the sample.

13. A method for inhibition of angiogenesis in a subject in need thereof, comprising administrating a pharmaceutical composition to the subject, wherein the pharmaceutical composition which comprises an anti-VEGF single-domain antibody of claim 1 and one or more pharmaceutically acceptable carriers.

* * * * *